(12) United States Patent
Tribelsky

(10) Patent No.: US 8,088,289 B2
(45) Date of Patent: Jan. 3, 2012

(54) METHOD AND DEVICE FOR AFFECTING A CHEMICAL OR MECHANICAL PROPERTY OF A TARGET SITE

(75) Inventor: Zamir Tribelsky, Mevaseret Tzion (IL)

(73) Assignee: Atlantium Technologies Ltd., Beit-Shemesh (IL)

( * ) Notice: Subject to any disclaimer, the term of this patent is extended or adjusted under 35 U.S.C. 154(b) by 0 days.

(21) Appl. No.: 10/522,315

(22) PCT Filed: Jul. 27, 2003

(86) PCT No.: PCT/IL03/00621
§ 371 (c)(1),
(2), (4) Date: Sep. 22, 2005

(87) PCT Pub. No.: WO2004/011038
PCT Pub. Date: Feb. 5, 2004

(65) Prior Publication Data
US 2006/0104859 A1  May 18, 2006

(30) Foreign Application Priority Data
Jul. 25, 2002 (IL) .......................................... 150914

(51) Int. Cl.
*C02F 1/32* (2006.01)
*A61L 2/00* (2006.01)
(52) U.S. Cl. ........... 210/748.11; 210/748.01; 210/748.1; 422/22; 422/24
(58) Field of Classification Search .................... 422/24, 422/22; 210/748.11, 748.1, 748.01
See application file for complete search history.

(56) References Cited

U.S. PATENT DOCUMENTS

| 3,264,055 A | | 8/1966 | Barker | |
| 3,503,804 A | * | 3/1970 | Schneider | 134/1 |
| 4,009,382 A | | 2/1977 | Nath | |
| 4,676,896 A | * | 6/1987 | Norton | 210/192 |
| 4,749,126 A | | 6/1988 | Bruls et al. | |
| 4,816,145 A | | 3/1989 | Goudy, Jr. | |
| 4,952,771 A | * | 8/1990 | Wrobel | 219/121.67 |

(Continued)

FOREIGN PATENT DOCUMENTS
DE       43 07 204 A    9/1994
(Continued)

OTHER PUBLICATIONS

U.S. Appl. No. 60/330,174; Saccomannno, Robert J., Apparatus for Disinfecting Water Using Ultraviolet Radiation, Oct. 17, 2001.*

(Continued)

*Primary Examiner* — Kevin Joyner
*Assistant Examiner* — Regina M Yoo
(74) *Attorney, Agent, or Firm* — Pearl Cohen Zedek Latzer, LLP

(57) ABSTRACT

A method and device are presented for affecting at least one chemical or mechanical property of a target site (109). A stream of liquid towards a contact with the target site (109) is provided with a predetermined flow rate. Also provided is UV-radiation (103) having predetermined parameters in terms of power, wavelength, duty cycle and repetition rate. The UV-radiation (103) is directed within the stream of liquid (101) along a trajectory of the stream. The stream carrying the UV radiation is maintained in contact with the target site for a time period and under conditions sufficient for affecting the at least one chemical or mechanical property.

5 Claims, 5 Drawing Sheets

U.S. PATENT DOCUMENTS

Figure 1:
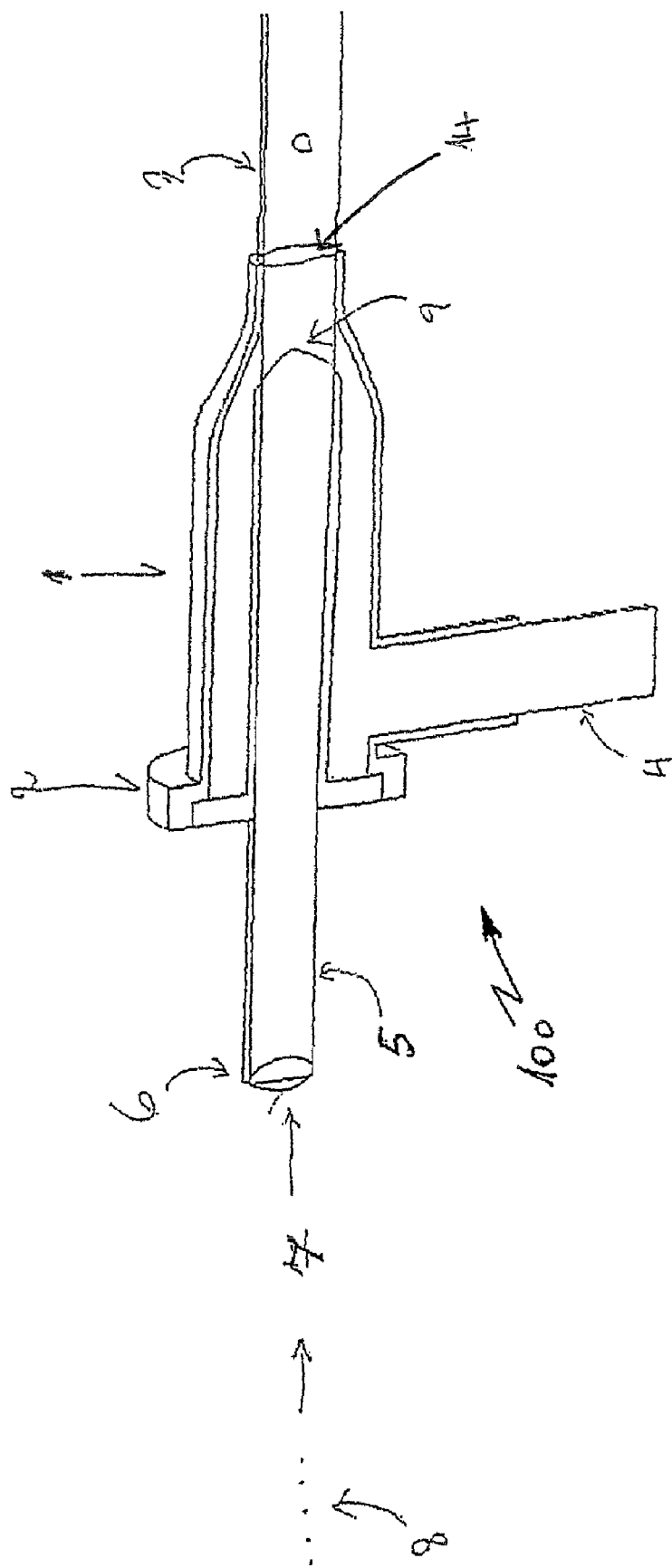

| | | | |
|---|---|---|---|
| 5,412,750 A | 5/1995 | Nath | |
| 5,546,493 A | 8/1996 | Noguchi et al. | |
| 5,658,148 A * | 8/1997 | Neuberger et al. | 433/215 |
| 6,163,641 A | 12/2000 | Eastgate | |
| 6,314,226 B1 | 11/2001 | Nath | |
| 6,418,257 B1 | 7/2002 | Nath | |
| 6,468,433 B1 * | 10/2002 | Tribelski | 210/748.06 |
| 6,507,688 B1 | 1/2003 | Nath | |
| 6,773,584 B2 * | 8/2004 | Saccomanno | 210/205 |
| 2002/0079271 A1 * | 6/2002 | Baca | 210/748 |
| 2004/0020862 A1 * | 2/2004 | Baca et al. | 210/748 |

FOREIGN PATENT DOCUMENTS

| | | |
|---|---|---|
| WO | WO 85/05167 | 11/1985 |
| WO | WO 95/29300 | 11/1995 |
| WO | WO 00 32520 A | 6/2000 |

OTHER PUBLICATIONS

U.S. Appl. No. 60/364,509; Baca et al., Laser Water Detection, Treatment and Notification Systems and Methods, Mar. 14, 2002.*
International Search Report for PCT/IL 03/00621.

* cited by examiner

METHOD AND DEVICE FOR AFFECTING A CHEMICAL OR MECHANICAL PROPERTY OF A TARGET SITE

CROSS-REFERENCE TO RELATED APPLICATIONS

This application is a National Phase Application of PCT International Application No. PCT/IL2003/000621, International Filing Date Jul. 27, 2003, claiming priority of Israeli Patent Application 150914, filed Jul. 25, 2002, both incorporated by reference herein in their entirety.

FIELD OF THE INVENTION

The present invention is generally in the field of radiation transmission techniques, and relates to a method and device for guiding UV radiation to a target site. The invention can be used for various photochemical treatments, for example aseptic filling of liquids into containers.

BACKGROUND OF THE INVENTION

Optical device operable with the deep UV and other regions of the electro magnetic spectrum (UVA, UVB, UVC, VIS, NIR, IR) have been of interest for many years. Most of the conventional available optics are not able to whithstand the great energy and thermal dynamics associates with cooling a high-power light beam to water, air, or combination of liquids and gases. Most types of glasses have been tried, and wide varieties of high grade fused silica are available to deliver deep UV light. However, these elements are expensive, and are limited to the energy levels that could be delivered. Further more, spatial limitations and damage threshold limitation have been imposing strict limitations as to the ability of quartz type and synthetic glass elements to deliver the energy levels often required for commercial material processing, lithography, and photo induced chemistry. More specifically, strict limitations to produce a UV reflective coating, have hindered progress in this field, leaving many spatial processing only available from quartz 7 and expensive optical grade polymers, and crystals, all of which are mainly used for processing and manipulating light beams in other spectral regions, such as can be seen in the VIS, NIR, IR (i.e., such as in telecomm, & IT).

Powerful or accurate light sources (including one or more lasers, or hybrid light sources including lamp(s) and laser(s)) often require expensive optics and optical grade manufacturing methodologies using HGFS (High Grade Fused Silica), SHGFS (Synthetic Fused Silica), and expensive semi-conductor coatings often applying several layers of AR/RC (Anti-Reflecting/Reflecting type coatings). Devices using such light sources are subject to physical limitations, photo damage and deterioration affecting all optical components in the beam path and thus often cannot reach the desired performance parameters, damage threshold, and physical properties associated with truly industrial, continuous, repeatable operation. These limitations have dictated to designers, producers and end users to integrate expensive cooling units negatively effecting energy consumption, wall plug efficiencies, increasing periodical maintenance and replacements, while increasing capital cost associated with devices using currently limited methodologies, such that are effected by thermal dynamics and optical damage thresholds.

Current evolution in laser, electro optics, electronics, and solid state electronics have pushed energies higher, and increase substantially time domain optronic manipulation capabilities (i.e. creating more peak power densities), and increase demand for wide variety of coupling, switching methodologies. Currently used optical grade production techniques rely on high temperature, skilled engineering, and considerable infrastructure, and energy demanding production sites limiting the scope and commercial and industrial high power laser applications, laser induced photochemistry, and material processing applications requiring lasers operating at high average, high peak powers, often at very high repetition rates.

Currently used production methodologies for high grade optical elements mainly utilize high energy driven temperature generators, heavy machinery, heaters driven mold processes, furnaces, often pause safety threats, and expensive surface processing, and coating treatments for polishing the finished element or lenses.

Current commercial efforts aimed at manufacturing such high damage threshold UVC optics, have failed to provide industrially acceptable high quality, high damage threshold, optical grade UVC optics and repeatable optronic processing free of thermal conventional limitation of optical grade materials.

Several technologies exist for the provision of surface treatment applications. These currently used technologies introduce strict safety, reliability, and credibility and efficiency limitations due to their chemical, residual, often toxic, expensive, slow, labor and material driven procedures and processes. Further more, current methodologies for surface treatment of instrumentation is cumbersome, and could not easily be adapted to cover applications requiring actual treatment of physiological damage to tissues, and/or for cuts, sores, wounds, to living human beings. Further more, in the field, or as in during critical medical procedures under time constraints, wherein often there is no sufficient time available to wait for certain chemical action to proceed (such as when using biocides, or chemical disinfectants), or for instrumentation to be returned from central, often far autoclaving, and disinfection equipment centre (i.e. such as in hospitals, and medical centers, or clinics), failed to provide adequate safety measures for vital tools and instrumentation, often results in making their associated working cycles longer, less efficient, requiring substantial replacement hardware components, and leads to unnecessary manual procedures, and subsequent expenses in human resources, and high energy consumption (high capital, and operation costs) as well as potential failure of vital medical procedures.

Most medical instrumentation is in need of sterilization, or disinfection leaving bacteria, and/or noxious species at a sufficiently low concentration according to standards, health, and safety regulations. Further more, medical instrumentation used in wide variety of medical procedures is currently being treated with chemical disinfectants. As heat already being considered as one of the most expensive disinfectant, or sterilizing methodology often requiring long and wasteful work cycles schedule. More specifically, the long time cycle chemical disinfectant takes for effective inactivation of DNA & RNA replication sequences or for oxidizing thus inactivating noxious species fuels the drive for new more efficient, non chemical methodologies.

Currently used methodologies utilizing UV light for disinfection, and photo-treatment is making use of (CW) Continuous Wave, often polychromatic light sources, most of which having radial emission, and not sufficient peak power (i.e. such as generated by P.W. type light sources). More specifically, the principle means for the generation of Ultra Violet light for disinfection and for photo-treatment is by using Mercury type light sources, or lamps. These lamps generate continuous type of light (i.e. CW), and the majority of the light they generate (their peak emission) (mercury) is at the region of about 254 nm. These light sources/amps, thus do not have the required wavelength for offering efficient disinfection, and sterilization of wide varieties of medical instrumentation. More specifically, current methodologies for disinfection and sterilization of medical instrumentation include heat, Gamma rays, X-rays, Y-rays, radio waves, Ultra Violet, microwaves, chemicals. These methodologies while offering currently implemented solutions, imposed strict limitations on the device performance.

Conventional treatment technologies available today include: Heat, ozonation, chlorination, oxidation, Gamma rays, X rays, Y rays, UVA, B, C photons, radio waves, microwaves, and several types of ionizing radiation, oxidation technologies, AOTs (Advance Oxidation Technologies such as using H2O2/UV, TiO2). These currently used treatment technologies are often dangerous, expensive, and require substantial periodical maintenance and replacements. Furthermore, instrumentation using such ionizing radiation types requires sophisticated support means, and infrastructure safety measurements, further complicating design criteria, and implementation. Several of these radiation types have already confirmed as causing cancer, and public confidence in these technologies at manufacturing plants is declining. Stringent legislation and standards further fuel the need for alternative, safer, more economical methodologies for non interfering treatment. Conventional chemical technologies are limited since there is always the need to clear the liquids and gases (of the "harmful" chemicals), and remove them from the specific volume to be consumed (i.e. after disinfection, or purification have occurred) once they have finished their useful cycle, or their disinfection, and oxidation activities.

The present invention takes advantage of the known technique of guiding light, especially UV radiation, via a liquid medium (e.g., water). Guiding light inside water has been used for the purpose of decorative functional fountains and illuminated falls, such that can be found in ancient and/or modern architecture. Various waveguides for transmitting UV radiation have been developed and are disclosed for example in the following U.S. Pat. Nos. 4,009,382; 5,412,750; 5,546,493; 6,163,641; 6,314,226; 6,418,257; and 6,507,688.

The use of a liquid jet or stream to conduct light has been proposed. For example, WO 85/05167 discloses a liquid outlet adapted to provide lighting effects and/or for illumination, that may be used in the fields of domestic plumbing ware as water taps, faucets, drinking fountains; ornamental and display fountains; beverage dispensers; in laboratory or industrial processes. According to this technique, light of arbitrary wavelength(s) is introduced into a jet or stream of liquid, either hollow, solid or subdivided, such that this light is totally or partially conducted by the jet or stream. A light source organ is placed inside the liquid-stream close to the outlet, such that the light source organ is in heat exchange relationship with the liquid flowing through the outlet and the light output into the liquid stream is maximized, or at a distance from the outlet but optically coupled to that outlet along any curved or bent pathway by means of some auxiliary light guiding mechanism.

WO 95/29300 discloses an apparatus and method for introducing electromagnetic waves (especially visible light and infrared or ultraviolet light) into water or water streams in sanitary installations such as shower systems, tabs and bath tubs. When the electromagnetic waves are visible light, the illumination of water takes place in one or combination of two forms: illumination by light reflection from the turbulent or broken water streams and illumination by light carried by the unbroken water streams or waters, where the electromagnetic waves being introduced into the water streams are able to be carried and guided by the water streams because of higher optical refractive index of the water compared to the air. Part of sanitary installations such as part or whole of the shower head is illuminated by the light sources. The colours and/or patterns and/or the intensities of the light source is able to be adjusted manually or automatically according to certain water conditions such as the temperature or the flowrate/pressure or cleanness of the water in use. The optical source is placed at the shower/tap head or separated from it. In the latter case, reflective mirror means or optical wave guide means or fiber optic means is used to guide the optical energy from the light source to the appropriate water streams. When the light source resembles sun light, combined sun bathing and shower unit can result.

SUMMARY OF THE INVENTION

The present invention discloses a novel methodology for combining a liquid medium with light for the purpose of creating a flowing liquid light guide.

The present invention provides a method for executing a certain processing (e.g., chemical treatment or mechanical treatment) through a jet or stream of light transmitting liquid. According to one broad aspect of the invention, there is provided a method for affecting at least one chemical or mechanical property of a target site, the method comprising:
 (a) providing a stream of liquid having a predetermined flow rate towards a contact with the target site;
 (b) providing UV-radiation having predetermined parameters in terms of power, wavelength, duty cycle and repetition rate;
 (c) directing said UV-radiation within said stream of liquid along a trajectory of said stream;
 (d) maintaining said stream in contact with said target site for a time period and under conditions sufficient for affecting said at least one chemical or mechanical property.

The liquid stream may be free-space flowing along at least one portion of its trajectory.

The target site is an item or a substance suspected as afflicted by noxious biological or chemical species. The target site is selected from profiled containers, filled containers, surfaces, humans, mammals, vehicles, medical instrumentation, conveyors, conveyor belts, foods, fruits, vegetables, salads.

The UV-radiation is generated by a laser source, which is preferably a high-frequency pulsed laser. For example, the laser source is a pulsed 266 nm laser, or pulsed 355 nm laser. The laser source may be a high intensity sub-microsecond pulsed laser.

The technique provides the chemical or mechanical change applied to at least 50 percent of particle type or microorganism species predetermined as a subject for having the change.

The same UV radiation carried by the stream of liquid performs may be used for the disinfection of the liquid on its way to the target site.

The method may comprise recycling the liquid by gathering it from the vicinity of the target site and returning it towards another contact with a target site.

More specifically, method comprises the following steps:
 (a) generating at least one light beam having wavelength, intensity and duration selected to be effective for the initiation of the treatment;

(b) forming at least one unpiped jet stream of light transmitting liquid, said jet having a predetermined launching point, trajectory, and target site, said liquid having a refractive index ($N_1$) greater than a refractive index ($N_2$) of the surroundings of said jet;

(c) directing said light beam into said jet such that said light beam is being guided throughout said jet, locked within along its trajectory towards the target site;

thereby enabling said treatment by said guided beam in between the launching point and the target site.

Various types of photochemical treatments may utilize the new innovative method of the present invention, all of which are based on the same novel advantageous principle of using an unpiped liquid jet as a "flowing wave guide" for light radiation adapted to the specific required treatment. These various type treatments, their advantages comparing to corresponding treatments using conventional existing methods, and the ways for performing them will be further explained in detail.

According to the present invention, a novel methodology is disclosed, for non destructively coupling high intensity beams of light in the germicidal range (220-380) to flowing liquid and gases thus creating a real time flowing liquid wave guiding methodology and for spatial processing using flowing suspended liquid formation having a higher refractive index therein, then the refractive index of the space, air, gas or liquid surrounding it. More specifically, triple guiding; (a) said light spatially locking it inside the flow homogeneously so as to fit variable boundaries formed of a continuum of refractive index profile between said (b) flowing liquid having a higher refractive index (1.33) therein then the (c) air or gas outside it (normally 1.00), and liquid and gases hydraulic, and pneumatic interactions (shapes, and variable space dimensions) into hydro optical fusion geared for photo-induced chemistry, and for sterilization and disinfection of liquids and gases, water, and air or surface combinations.

The present invention provides a novel methodology for creating a real time flowing liquid wave guide or photochemistry. According to this technique, output from at least one radiation unit having a high intensity pulsed sub-microsecond laser UV light beams is inserted or coupled into an input opening in a hollow aerobic, non toxic, liquid (water) projection means. The latter is a conduit or a chamber having integral conductive, dielectric, semi conductive or super conductive link having at least one inlet and an outlet launcher shaped for dynamic hydro-optical and photochemical predetermined processing effects. Said conduit or chamber has at least one opening un-hindered for passage of liquids and light simultaneously throughout. Each of said openings is equipped with optical input or output having predetermined diameter, acceptance angle and biocompatible or photo catalytically immobilized inner or outer surface area layer or thin film coating and at least one venturi suction point sufficiently large for light to be inserted through said opening passage, and sufficiently small for the liquid to remain inside flowing forward in a continuum of laminar or turbulent or combinations flow formats. A predetermined volume of liquids or gasses or combination thereof is pumped simultaneously through said inlet of said liquid projection means to be processed or triggered by the interactions of said guided light. At least one jet stream with a refractive index N1 higher than a refractive index N2 of the air or gas surroundings (e.g., N1=1.3 and N2=1.00) is launched forward simultaneously, such that said jet streams form a refractive index profiles N1/N2 with its surrounding, adequate for guiding said pulses of light by total internal reflection. The jet stream may contain at least one bubble. A continuum of predetermined volume of said liquids, and gases are delivered simultaneously to said outlet launcher positioned further along said hollow water projection means, at a predetermined pressure volume, or flow rate or combination sufficient for the formation of at least one venturi pressure point at said non hindering opening eliminating the need to use solid state optical grade elements or lenses, reducing the number of elements in the optical path length from air through water to surface reducing attenuation, increasing damage threshold, reducing periodical maintenance and replacements. A predetermined oxygen concentration, or singlet oxygen species, or predetermined oxidizer, or photo-catalytic semi conductive metal, or metal oxide particles, or nano porous, or non porous multi-components or semi conductive or dielectric combinations may be added or subtracted to the flowing liquid jet stream proportionately so as to form radical species or for photolytic, or photo catalytically triggering or for directly photo chemically effecting disinfecting, or sterilizing, dissociating, mineralizing or oxidizing, cleaning or decontaminating said liquid or gases or surfaces or combination in a single simultaneous action within a predetermined period of time.

The invention is especially beneficial for disinfection through the skin of internal blood flow (using the flowing liquid waveguide of the present invention), and bodily fluids without causing any damage, for treating medical instrumentation and engineering tools with pulsed UVA, UVB, UVC laser light guided by the UVJET of the present invention—where the geometrical curvature is often difficult to reach using conventional disinfection, or purification technologies. The method of the present invention can also be used wherein the cork, or lid themselves are made of polymer varieties having higher refractive index then the liquids, and/or gases therein (i.e. in the packaging), in order to maximize geometrical utilization.

More specifically, the UVJET of the present invention may be easily scaled up or down modularly. As an example; the methodology of the present invention for surface treatment is also beneficial for improving the hygiene of the mouth by harnessing the illumination or irradiation of a wave guiding dielectric brush [WDB] sterilizing its complex curvature inner surfaces, and volumes, having variable depth of penetration catalytically using new generation of paste, comprising:

Constructing or integrating a multi-component compound structurally modular, containing predetermined portion of yielding Oxygen Charge (SYOCH) in a U.P.W, PH stabilized, held temporarily or permanently in a 3D polymeric frame work of biodegradable biocompatible carbomer or Bi-polymers expanded to contain photo-catalytic, and, or centilating conversion elementally each having predetermined electron charge transfer co.-efficiencies and absorption, refractive index profile, and acoustic properties, selected pre-production for quantum objective application specific efficiencies driven thus from supper conductive, to dielectric, or semi conducting, wherein the flexibility of water may provide generic structurally yielding Oxygen Charge accommodating into manageable forms the decomposed species inactivated radically (SYOCH1), within water, liquid or gas or air suspension, body fluids, or inside mouth using new generation of paste according to the methodology of the present invention.

The device may be used for dentistry, general dentists, perio-dentists, orthodontists, exodontists, pediatric dentists, endodontists, oral/maxillofacial surgeons, and orthodontists, wherein the duty cycle of procedures thus performed in these respective field when using multicomponent catalytic U.PW based compound or coupling gel, spray, or liquid or gas facilitating the shortening, and time and resources saving, as results of effectively reduction of the population of noxious species on surface or volume, within predetermined area or dimension, thus increasing the level of health, and therapeutic applications of devices according to the methodology of the present invention. Duty cycle is a time period during which the laser beam is actually cutting, drilling, welding, or heat-treating, as compared to the entire work cycle time.

More specifically, the methodology of the present invention also relates to a catalytic tooth paste capable of scintillating or repeatable triggering by using visible, UVA, UVB, UVC, optical triggering signal eliminating the need for repeatable brushing. More specifically the present invention facilitates the dissolving of pluck formation catalytically, scintillating, and deep disinfection, and dissociation therapeutic effective treatment.

Considering the refractive index of water (1.3), and the refractive index of air (1.00), when light is coupled to a real time flowing liquid wave guide it gets locked, and reflected by T.I.R (Total Internal Reflections) thus creating a light jet (UVJET) according to the methodology of the present invention.

In the context of the present invention VOCs reduction means reduction of Volatile Organic Compounds by the use of a flowing liquid wave guide (could be used also for TOC reduction in the same principle)

In the context of the present invention Virus means a sub-microscopic microbe that causes infectious disease. A virus can reproduce only in living cells.

The usual wavelength range in Photochemistry is 100-1000 nm. Light photons with wavelengths longer than 1000 nm have a photon energy too low to cause chemical change when absorbed, and photons with wavelengths shorter than 100 nm have so high energy that ionization and molecular disruptions characteristic of radiation chemistry prevail. The total wavelength range is divided into bands with specific names as given below.

Spectral range naming in the context of the present invention (in nanometers):

| Range Name | Wavelength |
|---|---|
| Near Infrared | 700–10000 |
| Visible | 400–700 |
| Ultraviolet | 100–400 |
| UVA | 315–400 |
| UVB | 280–315 |
| UVC | 100–280 |

Little photochemistry occurs in the Near Infrared. Except for some photosynthetic bacteria, which are capable of storing solar energy at wavelengths out to 980 nm, the Visible range is completely active for photosynthesis in green plants and algae. Also many dyes can undergo photochemical transformations themselves or sensitize reactions in other molecules. Most studies in photochemistry involve the Ultraviolet range. The division into three sub-ranges [UVA, UVB, UVC] is associated with the human skin's sensitivity to ultraviolet light. The UVA range causes changes in the skin that lead to sun tanning. The UVB range can cause sun burning and is known to eventually induce skin cancer. The UVC range is extremely dangerous since it is absorbed by proteins, RNA and DNA and can lead to cell mutations and/or cell death. The UVC range is sometimes called the "germicidal range", since it is very effective in inactivating bacteria and viruses. The Vacuum Ultraviolet range is absorbed by almost all substances (including water and air).

Thus it can only be transmitted in a vacuum. The absorption of a VUV photon causes one or more bond breaks. However, even though photons with wavelengths less than 561.6 nm are capable of splitting the $H_2O_2$ molecule, no photolysis, or proteolysis occurs in this wavelength region because $H_2O_2$ does not begin to absorb ultraviolet light until below 300 nm. This illustrates the first Law of Photochemistry; namely that no photochemical reaction can occur unless photon(s) of light is absorbed.

In the context of the present invention, coherent and incoherent light means light sources used in photochemistry that can either be coherent (all emitted photons are in phase with each other as they propagate) or incoherent (all emitted photons have random phases). All lasers emit coherent radiation and usually at one wavelength. The dispersion is very small so that a laser beam remains at or near its original diameter as it propagates; the light emitted by all other light sources is almost always incoherent. Most of these sources are either "hot element" sources (e.g., incandescent light bulb) or "plasma" sources (e.g., a fluorescent light tube).

In the context of the present invention, "point source" means light sources that have finite dimensions (e.g., often a cylindrical shape). Emission from such a source is difficult to treat mathematically. It is convenient to mode these sources as a collection of point sources, in which all light is emitted from the point equally in all directions. The optics treatment for point sources is especially simple.

In the context of the present invention, the terms and concepts associated with the emission of light, are herewith included for clarity of explanation and to simplify the understanding of the method of the present invention for real time flowing liquid wave guiding (of light and liquid simultaneously), especially wherein photochemistry is involved, or photochemical polishing (meaning enhancing an already implemented processes such that a larger treatment objective is achieved) is active in the processing according to the present invention:

The light emitted from a source can be viewed in many different ways. In this Section, the various terms that may be used to describe this emission are defined and explained.

Radiant emittance or excitance: The Radiant emittance or excitance of a source is the radiant power emitted from an infinitesimal area on the surface of the source.

Radiance: Radiance (L) is defined as the radiant power $d^2P$, emitted from an infinitesimal area dA of the source surface in a given direction about the solid angle di, divided both by the solid angle di and the orthogonal projected area.

The emittance M from an infinitesimal surface element dA is obtained by integrating L in spherical polar coordinates over the hemisphere of all outward-bound directions above dA.

An isotropic light source is defined as one in which the radiance L is uniform over all Outward directions. Terms and concepts associated with the receipt of light when light is emitted from a source, it radiates outward at the speed of light, when it impinges on an object, and it may be reflected, transmitted or absorbed. There are several terms that relate to the receipt of light.

Fluence Rate: Fluence Rate (E) ($W/m^2$) is the radiant power of all wavelengths passing from all Directions through an infinitesimally small sphere of cross-sectional area d, divided by CM Irradiance: Irradiance (symbol E; units $W/m^2$) is defined as the total radiant power of wavelengths incident on an infinitesimal element of surface of area as containing the point under consideration divided by as. The following are some important points regarding characteristics and differences between "irradiance" and "fluence rate":

Examples: For a parallel and perpendicularly incident beam, not scattered or reflected, irradiance and fluence rate becomes identical. For any UV source within a three-dimensional volume, the integration of UV irradiance over the interior surface of the volume, normally yields the UV power of the lamp. This is not true for UV fluence rate which characterized the use of sub-microsecond pulsed UV lasers in accordance with the methodology of the present invention for UVJET real time flowing liquid light guide.

The appropriate term for UV disinfection is "UV fluence rate" because a microorganism can receive UV power from any direction, especially when there is more than one UV lamp in the vicinity. In general usage, the irradiance or fluence rate may be expressed as MW cm^(-2). The irradiance is often incorrectly termed "light intensity". the proper definition of "radiant intensity" (I) (W sr^(-1)), is the total radiant power P emitted by a source in a given direction about an infinitesimal solid angle.

In the context of the present invention, Light Dose or Fluence means the light dose or fluence (symbol H. units J m$^2$) is the total radiant energy of all wavelengths passing from all directions through an infinitesimally small sphere of cross-sectional area dA, divided by dA. It is given by the average fluence rate times the exposure tune in seconds. The term UV dose is often used in UV disinfection literature. It represents the UV exposure of a given organism in the germicidal range.

Spectral units: All of the terms for tight emission or incidence refer to all relevant wavelengths. One can define spectral derivatives for each of these terms. For example, the light power emission of a LIV lamp is often expressed as the spectral power (W nm^(-1), defined as the power output in a narrow wavelength band divided by the width of the band. The solar spectrum received at the Earth's surface is described in terms of the solar spectrum irradiance. Also the spectral distribution of a lamp emission is often given as a plot of spectral power versus wavelength.

Photon based units: Photochemistry involves the interaction of photons of light with molecules and means: the definitions units that are based on photons.

Photon irradiance, photon fluence rate and photon flow: Each of the spectral terms can be convened to a corresponding equivalent photon flow and fluence rate by dividing the term by the average photon energy in the narrow wavelength band.

In the context of the present invention Quantum Yield, means the quantum yield (unites) Q is a measure of the photon efficiency of a photochemical reaction. e is defined as the number of moles of product formed or reactant removed (P) per Einstein of photons absorbed In the context of the present invention Peak power means the energy generated when squeezing (i.e., such as when pulsing) electromagnetic energy in short duration of time, for example, a pulse of a given average energy and power—lasting, or having a pulse width of around 1 second (1 s) will generate several watts in peak power, a pulse lasting or having width of microseconds (ms) will generate peak powers reaching the kilo-watts scale, while a pulse lasting nano (ns) seconds will generate peak powers reaching into the hundreds of million of watts which is especially beneficial for purposes such as optical dissociation, optical inactivation, optical polishing, and optical secretion and spectroscopy for control and diagnostics, so in short the shorter the pulse duration the higher its respective peak power.

Multi-photon-absorption-processes means a process which when harnessed could be very beneficial for the photochemistry involved in the processing according to the present invention, for example when 10 mj of energy (250,000 photons) are projected into a liquid or gas, the time it takes this projection is very important, if these photons will be furnished over 1 second time domain, then it leaves sufficient time for the electrons in said liquid or gasses molecules to relax back to the relaxed state before an additional photon is absorbed, but if we apply these photons in a time domain of 5 nanoseconds, then we do not leave time for the electrons to relax and the process is called "multiphoton absorption" process, which is non linear in nature and yields much higher quantum yield, or efficiencies, or speed of the reactivation, or a more efficient methodology for optical treatment, processing and polishing A hybrid of light sources means plurality of light sources and wherein their total spectral emittance, or total spectral distribution, or their total irradiance will cause multiphoton absorption processes by means of super imposing their time domain (example: 1 light source is slow=1 s pulse duration, and additional light sources are very fast=5 ns laser for example), their total irradiance is great and beneficial for the processes of the method of the present invention to occur efficiently, further more, such hybridization could include lamps and lasers, lasers and flash lamps, or any combination of CW or PW type of light source working together, in synchronicity, and or sequentially or link or resolved by time domain manipulation for maximizing photonic interaction in matter, especially beneficial for triggering the catalytic scintillating elemental compound according to the present invention.

Photo catalysis means the use of energy of a photon of light to catalyze chemical reactions. More specifically, such reaction may include the decomposition of water into hydrogen, and oxygen, and the complete oxidation of organic contaminants in aqueous environments. More specifically, the first step in photo catalysis is for the catalyst material to absorb photon of light in order to excite an electron from the valance band (VB), to the conduction band (CB), thus creating electron-hole-pairs. Each species must then migrate to the surface before recombination occurs. If this condition is met, the electron can be transferred to a surface adsorbed molecule, reducing it. It is important to note that for the processes to occur efficiently (preventing pre-matured recombination of the electron-hole pairs), the rates of reduction and oxidation must be comperable. The position of the band edges is critical for each step of the process, a photocatalyst material which is stable in water is Titanium Oxide ($TiO_2$).

Electro catalysis similar to photo-catalysis described above, but, instead of photons, utilizes an electrical charge, through the use of semiconductor material which has been specially selected (its band gap) for the charge applied. For the context of the present invention, an electro catalysis stable in water is I.T.O, or known in its chemical name and signature Indium Tin oxide. Further more, it is especially beneficial to combine and operate both electro catalysis and photo-catalysis simultaneously, or serially, or sequentially or in unison, or each separate catalytic is triggered separately in order to maximize the collective efficiencies, thus harnessing and improving the performance of current and future catalytic technological evolution according to the methodology of the present invention. This process may be beneficially harnessed and simultaneously applied in unison or in sequences, or in step time or in any combination thereof. The method of the present invention also relates to detoxification and sterilization of surfaces from dangerous bacteria and chemicals contaminating the surface either through normal application or by hostile action (when used not for aseptic filling but for NBC decontamination applications (not shown).

The principle is combination of UVNIS light with photo catalytic materials in the context of a real time flowing liquid waveguide of the present invention.

The chemicals (oxidants, photo catalysts) will be sprayed/scattered in the form of liquid solution or suspension stream or droplets or cloud from one or more containers, with the light pulses synchronized so that illumination reaches the active chemicals in the right place (at or near the surface) at the right time. Pretreatment of surfaces with non-volatile materials such as $TiO_2$, $ZnO$, etc., is another mode of application of the various components of the invention.

According to the technique of the present invention, locked and reflected pulsed laser light beams in the UVA, UVB, UVC, X-Ray, and visible regions of the electro-magnetic spectrum are utilized. The pulse duration, width, or time is sub-microseconds, adhering to the conditions for 2nd order interactions between light and matter performing multi photon absorption processes, amplification, and spatially controlling the TIR (Total Internal Reflection) patterns of the delivered light within the jet stream. This is especially beneficial for treatment of liquids and surfaces, as light is locked reflecting in the jet stream and thus can provide a multi functional feature enabling washing, filling, sterilizing any conduit or chamber simultaneously. More specifically, the method of the present invention discloses novel methodology for aseptically filling bottles in the bottling industries, or for aseptically filling and simultaneously washing and disinfecting the inner walls or surfaces of bottles, conduits or chambers. More specifically, an array of UV jet (hereinafter referred to also as "UVJET") units, may be used for aseptic filling a plurality of bottles simultaneously, driven by a solid-state optical fiber harness for delivering adequate energy dose for each jet in arrays of jets or for single remote clean room or production halls requiring 100% electrical safety or high level of biocompatibility. Especially beneficial for disinfection and aseptic filling of bottled water, mineral water, flavored water and beverage and agro-food industries. Furthermore, the method of the present invention is especially beneficial for bio-photonic and biomedical applications wherein light can be delivered externally or internally (in vitro or in vivo) within the flowing jet stream of UPW (Ultra Pure Water with reduced TOCs, VOCs) class water jet or any water based suspension. This facilitates the ability to remove catalytically (photocatalytically or via photochemical process) tumors and excess or unwanted pluck formation (within main Aorta) or remove smoothly restenosis, tissues or sterilize area or dimension or liquid such as blood or water, or gas such as air or oxygen or combinations as well as disinfect surface such as human skin or tissue, polymers. The methodology of the present invention is also beneficial for washing and disinfection and advanced oxidation of human skin from BW, CW eventualities, or for the protection and cleaning of metropoolitan areas from biological and chemical contamination.

The present invention provides for production of UVJET, (or a water stream carrying pulsed UV light or sprinkler, or jet or fall or vapor) wherein pulsed UV laser light beams are locked and guided in the flowing variable liquid geometry by total internal reflection (TIR) thus forming UVJET, or VISIJET, or X-RAYJET. More specifically, liquid (water) with a refractive index $N_1$ (e.g., 1.3) is flying, projected/rejected in space, i.e. in air, or from air to surface, wherein the air or gas surrounding the liquid jet has a refractive index $N_2$ (e.g., 1.00) lower than that of the liquid, thus creating a refractive index profile (interface) $N_1/N_2$ within the JET stream. As a result, light transferring the jet at appropriate angular orientation stays locked, reflecting in the jet stream itself. The time domain differences of (a) hydraulic non uniformities, and (b) pulse width, PW or the duration in which a pulse of light transverse the jet stream, facilitate many advantages in photo-induced chemistry according to the methodology of the present invention.

Creating internal reflection therein (i.e. sub-microsecond pulses reflecting in the jet stream) is especially beneficial for applications requiring surface, and/or dimension, volume, and wherein light for disinfection or detoxification, or purification of surfaces having complex curvature is performed efficiently. The UVJET concept is especially beneficial for guiding light therein (in the water, liquid or gas or combination) for wide variety of photo-induced chemistry. More specifically, such treatment may be initiated wherein the jet stream is dielectric, semi-conductive, or super conductive or any combination thereof which may maximize yields and efficiencies in photolytic, photo catalytic, or for advanced oxidation processes involving the formation of radical species (such as OH radicals for example). Furthermore, the methodology of the present invention facilitates the production of a beam containing high energy density zone, producing radical species, offering disinfection and washing in a single action radical may be produced by photolysis of Oxygen or by photo catalytic interactions formed as a result of adding semi-conductor metal oxides, or nano particles or suspension which creates electron pair holes when pulses of light having sufficient e/V are introduced reflecting within the UVJET stream. Furthermore, production of a UVJET wherein high peak power UVA, UVB, UVC pulsed sub-microsecond light is encapsulated within the flowing water stream (according to the methodology of the present invention), enables potent photochemical, photo catalysis, photolysis and photo-electro catalysis processes to be performed simultaneously or separately or sequentially or in combinations. More specifically, using the UVJET hydro-optic reactor architecture both producers and end users benefit. More specifically, no reflective coating or hardware reactor type are needed, no optical elements are required for replacement reducing periodical maintenance and replacement associated with current technologies using heat or ionizing radiation. Furthermore, time domain interactions within the real time flowing liquid waveguide of the present invention may be harnessed and monitored spectroscopically (i.e., in a spatially flexible geometrical variant reactor) architectures, all which are beneficial for programmable computer controlled photo-chemistry and photo treatment within the real time flowing liquid pulsed light guide the UVJET, VISIJET, X-RAYJET according to the methodology of the present invention.

The present invention provides for agricultural, environmental protection, disinfection, and sterilization, water and medical and biomedical and health related fields and for producing hydro-optical elements for laser industry and markets (hydro-optical means simultaneously processing light and liquid flow dynamics to create unique optical and photo-chemical effects). Furthermore, the methodology of the present invention discloses a novel architecture wherein lasing may occur without the need for cooling as actual lasing occurs within the flowing liquid being the cooling element itself. More specifically, the present invention discloses a novel water laser amplifier facilitating unique set of advantages in two main categories as follows:

The first category relates to the ability to surpass conventional thermal limitation in conventional light sources, for example, actual lasing interaction occurs within the liquid itself acting as cooling element thus no external or integrated cooling units are needed.

The second category relates to the ability to process and offer sterilization of liquids that is not available with conventional thermal pasteurization technologies, especially beneficial for bottled water industries for filling and for sterilization or disinfection of drinks, beverages, and agro-food products such as flavored drinks. The present invention also facilitates biocompatibility and purity required for water and liquids used in the biomedical and pharmaceutical industries or for producing ultra pure water (UPW) for electronic and chip manufacturing industries. The method of the present invention also relates to detoxification and sterilization of surfaces from dangerous bacteria and chemicals contaminating the surface either through normal application or by hostile action (when used not for aseptic filling but for NBC decontamination applications (not shown). The principle is combination of UV/VIS light with photo catalytic materials in the context of a real time flowing liquid waveguide of the present invention. The chemicals (oxidants, photo catalysts) will be sprayed/scattered (etc.) in the form of liquid solution or suspension stream or droplets or cloud (etc.) from one or more containers, with the light pulses synchronized so that illumination reaches the active chemicals in the right place (at or near the surface) at the right time. Pretreatment of surfaces with non-volatile materials such as $TiO_2$, ZnO, etc. is another mode of application of the various components of the invention.

A UVJET according to the methodology of the present invention is having unique variable parameters creating new and exciting spatial optical processing especially beneficial for manipulating light beams having high average powers, and high peak powers or qusi combinations. Such beams as those generated by today's modern lasers may be adequate to form 2nd order interactions such as those created by multi-photon absorption processes.

The methodology of the present invention surpassed current strict limitations by creating a flowing liquid waveguide in real time creatively assimilating hydraulic, pneumatic, electro-optic and photochemical effects simultaneously for purpose of sterilization, photo catalysis, photolysis, especially beneficial for environmental protection applications which does not necessarily require the stability and temperature stabilization and optical grade element effecting capital cost of laser engines and reducing the number of component in the beam path. The elimination of conventional optical elements substantially reduces the cost and periodical maintenance and replacements associated with conventional treatment technologies such as heat based sterilization, ionizing radiation and conventional electromagnetic radiation such as eradiation coming from lamps (mercury vapor lamps). Lamps are not generally good candidates for driving the UVJET of the present invention. The principle means for the generation of ultra violet light from lamps is using mercury vapor lamps. These lamps are self limited as they have radial emission, polychromatic wavelength and sport mostly continuous wave type of light. More specifically, conventional UV lamps require reflecting coating for the deep UV which is not available yet. More specifically due to the radial emission of these lamps it is impossible to harness their light efficiently and couple it to the UVJET, unless the light from the lamps is coupled to the jet stream externally or across its cross sections to increase photon flow, fluence rate. In line with the physical limitation of conventional UV lamps wherein the more pressure the lamp carry—the more energy can be produced, but not in he UV part of the spectrum (lamps carrying high pressure output more infra red IR and visible then UV). As pressure is reduced, the lamp produces much more UV, but with no power thus conventional UV lamps are not adequately positioned to operate the UVJET of the present invention classically, however hybrid combination involving sub-microsecond pulsed UV lasers and lamps are indeed beneficial for increasing photon fluence rates and increasing the background light in the jet stream through which pulsed UV laser light is being reflected simultaneously or sequentially or singularly or in combination.

As the limitations imposed by thermal co-eficiencies, and damage threshold prohibit progress in these beneficial research fields such as (a) conventional quantum laser developments, (b) FELs developments, and (c) solid state, diode pumped lasers, in view of current technological evolution taking place, thus involving several key industries the search for economical, industrial optical processing techniques, materials, and production methodologies is ever imminent, and important. The methodology of the present invention provides a unique and creative spatial optical manipulation, guiding, and projecting using a flowing liquid waveguide having a higher refractive index then the space surrounding the liquid flow, thus while in motion guide light therein (i.e. in the jet, stream, fall, flows or combination) for purpose of sterilization or lasing, photo catalysis or photolysis or combination for achieving the photochemical effect desired.

More specifically, by creating a refractive index profile wherein the flowing liquid refractive index is higher then the refractive index of the air (or gas, or combination) (or gas) surrounding it light is guided within the flowing jet stream. Furthermore the present invention facilitate the formation of high efficiencies in coupling light to surfaces having complex curvatures, and to the simultaneous motion, process co-eficiencies, and beneficiary advantages of washing, and disinfecting in a single action. Such efficient cleaning action and sterilization may be applied to wide varieties of surfaces, substrate materials, including the ability to reach, and cover (i.e. disinfect, sterilize, purify, trigger) complex surface curvatures. Such surface curvatures that can be found in medical tools, instrumentations, and wide variety of accessories from many industries including packaged water products such as bottles and jugs (bottles & 5 gallons jugs for example).

Refractive index value of water generally stands on 1.33 and wide variety of liquids exhibits refractive index which is higher then the refractive index of air, thus light projected or delivered accurately, according to the methodology of the present invention, will be guided through the flowing liquid jet, or distributed to the jet using optical fibers or other solid state optical waveguides or fibers (such as high grade fused silica or synthetic fused silica, HGFS, SFS, or photonic band gap crystals) or combinations. Light may also be diffused prior to entering the jet-stream, within the jet stream or after passing or transferring the jet stream by total internal reflections. For certain application using the UVJET according to the methodology of the present invention, treatment may be applied using the edge, or distal remote tip of the jet stream. For other applications, the UVJET stream itself may serve virtual reactor architecture wherein photochemical, photolytic, or photo catalytic processes and combination interactions are occurring being performed using the methodology of the present invention.

When the liquid is flowing, light coupled to the flowing waveguide is locked, reflecting by internal reflections (TIR). More specifically, the present invention also disclosed a novel methodology for treating surfaces with changing, and/or variable curvature parameters due to the novelty of locking beams of pulsed laser light in jets, falls, and water in motion thus forming geometries (hydraulic, pneumatic, electronic, and, electro optical, and photochemical interactions, and combinations) of water. Furthermore, the inventive creative progress embedded in the textual disclosure according to the present invention describes a novel interaction which further enhances time domain interactions allowing controllable maneuverability from 1st, 2nd, 3rd order optronic, electro-optic, and photochemical and photo biological interactions. A method for the production of catalytic liquids, and gasses jet forming plasma driven flowing liquid light guide, and all electro-hydro-photo catalytic devices for use thereof is especially beneficial for the production, coupling, distributing, and applying dose of a predetermined energy levels, within a predetermined space, over a predetermined time, but with the vital inclusion of a refractive index profile which encapsulate the light beams as they propagate throughout the path length of the flowing liquid(s). Furthermore, the invention provides the variable dimension of the specific liquid in motion (i.e. water/air) forming a refractive index therein for keeping, reflecting, and locking the UVB, UVC pulsed laser energy, maximizing its photochemical applications for the benefit and the protection of public health.

More specifically, as an example; the present invention may include photo catalytically initiating protection for inner space of the mouth, or for the removal of pluck formation from teeth or inner cavities sterilization and washing and cleaning simultaneously. More specifically, by forming a catalytic light barrier technology such that creates a "fire wall", or in simple words a hydro-optical drilling and sterilization effects may be produced using the UVJET of the present invention. Such cleaning lightjet for specific dental or periodontal procedures is most beneficial for medical and biomedical industries as it provides 100% electrical safety and extremely high levels of biocompatibility. More specifically, the present invention facilitates the formation of a flowing liquid (water) light guide (using deep UV) for specific photo catalysis interactions, or for photo induced chemistry, or for removing, and dissolving pluck in arteries or tooth, or residues, and for generally applying water and light combined for physio-optical interactions, and for photo-induced chemistry in vivo and in vitro.

The technique of the present invention provides for development of devices wherein no known noxious species may penetrate and replicate, (i.e. bacteria, viruses) and thus have no ability to infect (present invention causing inactivation of their DNA, and RNA replication sequences). The technique of the persent invention is especially beneficial for the removal of pluck formation in periodontal treatment, and in arteries, and in keeping maintaining, and repeating triggering photo catalytically, photolytic, or by centilating processes causing appropriate triggering of $H_2O_2$, or $TiO_2$, or $TiO_2$/ITO or combination of photo-catalytic semi conductor coatings, or substrates, or surface encapsulation. This treatment provides for oxidizing predetermined noxious species which may inhibit the surfaces curvature, and the deeper layers, and volume surrounding the mouth area, body parts, inlets, or outlets, conduits, and chambers, or surfaces and volumes. With the technique of the present invention, such catalytic, and/or photo catalytic interactions may be triggered by a UVJET, or a flowing liquid waveguide able to deliver the right level of dissolved oxygen, stabilize PH, and offer powerful delivery medium for photo catalysis interactions (i.e. such as may be selected according to application requirements, H2O2, TiO2).

More specifically, wherein cuts and sores to body external surface, may cause damage to external body parts/tissues, and thus open the potential for infectious events entering the body, such events introduce potential threat of contamination, and cross contamination through use, and thus the methodology according to the present invention offers the realization and harnessing of advance catalytic oxidation technology facilitating uncontestable technological advantages due to the fact that the boundaries of the flowing liquid light guide are reflecting deep UVB, UVC, UVA pulsed laser light thus allowing a specific photon of light to transverse more efficiently to a given geometry, molecule or target organism. Use of the UVJET enhances the probability for 2nd order interaction (i.e. multi photon absorption processes). These non linear effects greatly accelerate the rate of photochemical processes in aqua suspensions, water, or any liquid or gas or combination and surpass limitation of conventional 1st order interaction driven treatment processes currently available using a continuous wave UVA, UVB, UVC (CW) often with polychromatic spectral characteristics, normally offered by CW UV lamps.

The methodology of the present invention utilizes the ability to couple light from sub-micro second pulsed UV lasers operating at high average powers, and high peak powers, often at high repetition rates. Hence, the technique of the present invention does not require optical windows, lenses, and additional optical elements normally associated with spatial optical processing in the UV range, at such high powers (sub-microseconds, yielding high peak powers, ns, ps, Fs, as pulse width PW or time domain).

More specifically, by preparing in advance all relevant parameters for efficient oxidation processes to occur (i.e. such as Oxygen, PH levels, stabilization, and the photo catalysts) in a tight cohesive, and homogenic and/or multi-component system or suspension, the present invention simplifies and guaranties photo catalysis processes in the presence of triggering energy density thresholds. The present invention provides competitive advantages when geometrically utilizing thoroughly space, and time, and light causing sterilization by pulsed ultraviolet (time domain driven) laser light for disinfection of wide variety of medical instrumentation and engineering tools by having the ability to guide light through a flowing liquid waveguide having a higher refractive index therein (i.e. in the jet stream, fall, or flow or combinations) then the refractive index of the surrounding space (i.e. air). Such refractive profile thus created (water at 1.33, and air at 1.00) causes light to be guided using total internal reflections (TIR).

The methodology according to the present invention is not so limited, that's why the present invention could be utilized for wide variety of application including but not limited to (a) treatment of ultrasound equipment (b) treatment of medical surgical procedures, (c) Dental treatment procedures, (d) Cosmetic procedures, (e) Gynecological procedures, (f) 1st aid treatment applications, (g) Bulk sterilization of tools and medical instruments, (h) Medical preparation, (i) Transplant procedures, (j) Diagnostic procedures, (k) By-pass operations, (l) Skin, and dermatological treatment procedures, (m) Chemical production sites for drugs, and medicine (n) Rehabilitation centers, (o) Hospitals, (p) Clinics, (q) Operation procedures in cancer treatment, (r) Medical procedures for birth, and pregnancy diagnostics, and treatment, (s) Treatment of burns, (t) Treatment of cuts, bruises, wounds, (w) Treatment of areas exposed to radiation, (x) Treatment of packaging of medical preparation, and drugs production or analysis, (y) Treatment of surgical instrumentation, (z) Treatment of diabetes wounds, treatment of liters, and gallons conduits or chamber containers, and bottles of mineral waters, flavored water, return lines of mineral water containers, beverage conduits, and chambers, washing of ships, transport vehicles, disinfection of devices and tools for the medical fields, instrumentation, and for photo induced chemistry. The UVJET according to the methodology of the present invention is also beneficial for dissolving pluck formation in the main aorta, and for unblocking clogged restenosis and residual compounding volumes in stenting procedures or for enhancing artery cleaning procedures.

The present invention is also beneficial for cleaning applications such as Cleaning vehicles, Cleaning airplanes, cleaning ships, and busses, Lories, and semi-trailers, tankers on land, sea, and air. Further more, several applications illustrated herewith as having best mode for utilization of the methodology of the present invention wherein coupling of high rep rate, high peak powers, high average powers lasers into water is disclosed, eliminating the need to use expensive optical lenses, saving on periodical maintenance, and replacements of devices using the methodology of the present invention.

More specifically, such preferred applications clearly illustrate an important innovative solution wherein the size of the actual triggering light (or energy, and/or energy density) under no circumstances dictate the size of the catalytic "fire", or free radical species thus generated by the processes according to the present invention. The present invention provides a novel methodology for hybrid disinfection of surfaces, to disinfection of volumes, to static storage sites, to large installations treating high flow rates or complexes surface curvatures (i.e. 2D/3D) such as appearing to shape modern medical instrumentations, and wide varieties of engineering tools. More specifically, by guiding light in the flowing liquid light guide the high energies which normally (when using conventional optical elements) generate heat, limiting the scope, and power capacities of currently used coupling methodologies, the present invention generate no heat due to the fact that the light is transferring actual cooling element i.e. the water or liquid used. In simple words, the present invention facilitates the coupling of high power laser devices to liquids, and gasses eliminating the need to use conventional HGFS (High Grade Fused Silica, high purity glasses) quartz elements, instead it is possible according to the present invention to utilize water flowing. Given that the refractive index of water, and its transparency, when pure to the UVA, UVB, UVC bands of the electromagnetic spectrum further emphasis the novelty and inventive step of the present invention.

More specifically, the method of the present invention for creating a real time flowing liquid wave guide or photochemistry consists of the following steps: The output from at least one radiation unit having a high intensity pulsed sub-microsecond laser UV light beams is inserted into or coupled to an inlet (input opening) of a hollow aerobic, non toxic, water projection means. The latter is a conduit or a chamber having integral conductive, dielectric, semi conductive or super conductive link, one or more inlet and an outlet launcher shaped for dynamic hydro-optical and photochemical predetermined processing effects. This conduit or chamber has at least one opening un-hindered for passage of liquids and light simultaneously throughout and wherein each opening is equipped with optical input or output having predetermined diameter, acceptance angle and biocompatible or photo catalytically immobilized inner or outer surface area layer or thin film coating and at least one venturi suction point sufficiently large for light to be inserted through said opening passage, and sufficiently small for the liquid to remain inside flowing forward in a continuum of laminar or turbulent or combinations flow formats. A predetermined volume of liquids or gasses or combinations is pumpes simultaneously through the inlet or the water projection means to be processed or triggered by the interactions of the guided light. At least one jet stream having a higher refractive index $N_1$ (at about 1.3) than the refractive index $N_2$ of air or gas surroundings (of about 1.00), is launching forward simultaneously, such that the jet streams form a refractive index profiles $N_1/N_2$ with its surrounding, adequate for guiding the pulses of light by total internal reflection. The so-obtained UVJET stream is guided or delivering projected and simultaneously fills packaged liquids or undergoes sequential spatial processing, or said pulses and liquid are distributed directionally to a predetermined surface target site or to the liquid package having a refractive index $N_3$ lower or higher than the flowing liquid light waveguide. The jet stream may contain at least one bubble; delivering a continuum of predetermined volume of said liquids and gases simultaneously to said outlet launcher positioned further along said hollow water projection means at a predetermined pressure volume, or flow rate or combination sufficient for the formation of at least one ventury pressure point at said non hindering opening, eliminating the need to use solid state optical grade elements or lenses, reducing the number of elements in the optical path length from air through water to surface reducing attenuation, increasing damage threshold, reducing periodical maintenance and replacements. A predetermined oxygen concentration, or singlet oxygen species, or predetermined oxidizer, or photo-catalytic semi conductive metal, or metal oxide particles, or nano poruse, or non porous multi-components or semi conductive or dielectric combinations can be added or subtracted to the flowing liquid jet stream proportionately so as to form radical species or for photolytic, or photo catalytically triggering or for directly photo chemically effecting disinfecting, or sterilizing, dissociating, mineralizing or oxidizing, cleaning or decontaminating said liquid or gases or surfaces or combination in a single simultaneous action within a predetermined period of time.

Due to the UVJET ability to deliver light without the thermal limitation quantum conventional lasers suffer from (i.e. generation of heat, subsequent cooling systems currently in use and which increase dramatically the capital cost associated with conventional light sources), the methodology of the present invention may be used for the creation of water based lasers, amplifiers, and spatial processors using a flowing liquid waveguide according to the present invention. Examples include air based catalytic compound oxygen charged and triggered; catalytic globulin mixture wherein its best mode of being triggered is by at least one pulse of light being generated by a high peak power, high repetition rate laser; a catalytic compound lighter or heavier then air being triggered while in transition or drifting, and wherein its catalytic actions produces sufficient free radicals to efficiently dissolve toxic substances, traces, or any liquid or gas or combination containing noxious or poisonous nature; steam type catalytic multi-component compound produced on the ground or from a flying vehicle or plain, or propelled to/from different locations according to needs. Indeed, this is the goal of many scientist, biotechnologists, medical engineers, doctors, and surgeon to have tools for dealing with infectious events with the ability to reduce working cycle, periodical maintenance, and replacements, and offer a more efficient treatment methodology thus able to remedy larger portions of the population in need, and to offer enhancement to currently available socio-economical performance. The method according to the present invention presents competitive advantages, and important saving benefits especially for medical, biotechnological, hospitals, clinics, and agricultural, and industrial applications, thus enhancing the quality of life in the human sphere by having the ability to use the method of the present invention to create devices able to wash, and disinfect simultaneously. (Such that are illustrated by the UVJET, or flowing liquid waveguide, or spatial processors for the deep UVC from water).

Furthermore, the methodology of the present invention provides for a real time treatment methodology by pulse power triggering of photochemical, and/or photo-catalytically surface treatment processes, and further penetrative techniques (using surface treatment to trigger volume treatment). It is already known in theory that every material may oxidize or break down if energy is applied to it, having at least equivalent amount of energy as the one holding it's molecules and atoms together.

The methodology of the present invention provides for several techniques for performing light TIR (Total Internal Reflections, i.e. guiding light in the flowing stream of the liquid), offers the ability to keep operating equipment use in medical procedures safe at all times, and eliminates the need to replace expensive optical elements. The methodology of the present invention is also offering much quicker turn over, shorter working cycle, and the ability to ensure high level of biocompatibility, while turning noxious species on the surface of said medical instrumentation into more innocuous sources.

The present invention provides manageable forms in real time, especially beneficial for clean and safe ultrasound procedures (examples include: in biomedical applications, or in monitoring pregnancies) using photo catalytic water based carbomer coupling gel, and for the protection of wide variety of medical instrumentation using the UVJET according to the present invention. More specifically, equipment peripherals (such as ultrasound accessories or probes) could be washed, and disinfected/sterilized using the method of the present invention.

The method of the present invention is a non chemical, non residual treatment technology. By using a photo catalytic compound made out of water, silicon, and photo catalytic material, such as $TiO_2$, for example, the present invention provides for treating wide variety of surfaces (of medical instrumentation) in short time facilitating the formation of workstations. Devices using the method of the present invention provides for transferring pulsed laser light to a remote receptive interface, activating photo catalytic agent therein (in the coupling solution used). More specifically, the methodology of the present invention is using Ultraviolet light from about 200 nm to about 400 nm to activate the photo catalytic agent present in a water based coupling gel (normally made out of silicon/water solution). By exposing the thin film coating left on probes, and ultrasound accessories, or body parts externally wounded, or for cuts, to a plurality of laser pulses in the region of the UVA, UVB, UVC, the present invention triggers the thin film catalytically, and thus photo catalytically inducing beneficial photochemical processes (for example disinfection, and sterilization), thus purifying, disinfecting, and inactivating noxious species on the plurality of surface described above (i.e. such as the surface of the medical instrumentations, wounds, cuts, sores, or externally damaged body surfaces). Furthermore, according to the method of the present invention the laser pulses having germicidal wavelength, and sufficient e/V energy for the specific treatment required for a particular application provide mild dissociation effects and are beneficial for providing an active source of hydroxyl radicals (i.e. OH* radical species) to offer photo catalytic solution in the field, or in disaster areas, or in places wherein the population is exposed to unexpected conditions dictating medical procedures to be performed without the infrastructure normally associated with hardware equipment for disinfection (I. Such as autoclave, ovens, Gamma rays, Radio waves, X-rays, microwaves, heat, cold, Sonication).

The present invention provides for forming a flowing real time liquid wave guide for the delivery, and distribution, spatial processing and manipulation of pulsed UVA, UVB, UVC lasers operating at high powers for the purpose of disinfecting surfaces, volumes, spaces, and substrates, inner surfaces of containers, and wide variety of tools, instrumentations, and devices in medical, engineering, agricultural, and industrial washing and disinfecting simultaneously. Photo reactive disinfection of surfaces and beneficial disinfection, and treatment of wide varieties of medical instrumentation is possible using the method of the present invention. Additionally, it would be a preferred mode of operation to cover the washed, disinfected, sterilized and/or treated surfaces items using a thin-film coating, and activation on the surface of wounds, cuts, bruises, sores, damaged parts of external body surface), and in air, such as when infectious events may pause threat to humans, animals, and plants. Furthermore, by integrating into high purity water enriched with oxygen, and mixed with catalytic powder, or liquid, or gas, or light, the methodology of the present invention facilitates the formation of active free radical layer swiftly making the surface curvature/proximities sterilized. Noxious species on said surface are then inactivated, thus the surface is been made safe from infectious events, (bacteria, viruses, and other health threatening noxious species). The present invention is extremely beneficial for much medical application hence there are no need for actual physical touching, tiring, or swiveling of tissues, or there is no need for physically interfering with an already sensitive, and often critical medical treatment scenarios. The present invention facilitates the formation of a free sterilized zone extending to reach the entirety of the spread of said catalytic compound, naturally in line with environmental conditions such as wind, air compound, PH levels, dissolved Oxygen and other factors effecting photo catalysis quantum yield of efficiency.

Disinfection, purification, and sterilization and phototreatment by Ultra Violet light technology is well known. This technology is preferred due to its non residual, non chemical, and effective (wavelength range from about 220 nm-357 nm) inactivation of DNA & RNA replication sequences in wide variety of noxious species (such as bacteria, viruses, Cysts, and Pathogens).

The present invention is aimed at environmental protection, and the protection of public health, and tools associated with domestic industrial, medical, engineering and environmental fields. Coupling light non invasively into the flowing jet stream of liquids, and gases using pulsed power optronic technology in the UVA/B/C electro-magnetic spectrum, and associated hydro optically resolved and aligned peripheries, provides for no need of the conventional optical elements. The driving principle behind the technology is synchronized control of the time domain, and facilitating an interactive variable platform for guiding light, and for spatially processing light therein (i.e. in the jet. When appropriate dose of light is delivered into specified water forming flanged geometry, or predetermined surface area causing specific electro optical, and photochemical effects in said water, and the target contacted by the jet/beam extension, the method of the present invention offers simultaneously washing, disinfecting, sterilization, and dissociation capabilities in a single simple, creative platform, surpassing limitation imposed by the use of conventional optical grade lenses, and elements, eliminating thermal limitation, maximizing time domain interaction in the liquids, and gasses thus delivered, flowing through, or utilized therein (in the jet stream or flowing water).

More specifically, the present invention discloses a novel methodology for harnessing a multigradient refractive index profiles causing light in the relevant germicidal spectral regions to stay locked, guided, and reflected within the water of the get, stream, falls, sprinklers, or shower tub, or filtration system, especially beneficial for water treatment of drinking, wastewater, aquaculture, and water reclamation, water recycling, and water purification workstation driven applications and platforms. The present invention could be further utilized for surface disinfection, and purification, and for dimensional coupling light from about 1 mJ, to about 1 mw/Cm2 regime to the TW/Cm2, average power, and to peak powers reaching up to hundreds of billions of watts in cross sectional energy densities, and such high intensities are coupled to water according to the methodology of the present invention harnessing the quality of life through implementation of total bio-security for water and air, and other liquids and gases.

The present invention facilitates efficient socio-economical treatment platforms for the protection of public health and the environment by facilitating the catalytic formation of radical species (such as OH*) barrier technology (CFRS, ref 3 a-z), a layer which upon triggering turns to "fire wall" (thus preventing passage through of noxious species due to the short duration of time [Fs] in which the catalytic processes occurs) made out of multiple layers of highly radical species, lasting extremely short fraction of time, for the purpose of forming photo reactive layer wherein the preferred mode for advance Catalytic Oxidation, Electro catalytic Oxidation, photolysis, and photo dissociation (of upper surface layers of medical instrumentation, as well as actual damaged tissues of the Human body) occurs, the present invention by guiding light in a real time flowing liquid wave guide offers many advantages, remove thermal limitation, and provide an important socio-economical benefits helping protect mankind, and its environment.

More specifically, the present invention facilitates the provision of a protective photo reactive barrier technology (PPRBT), by means and utilization of light, liquid, gasses, and optronic time domain triggering (such as can be produced by high peak power high rep. rate UV lasers), increasing the probability for multiphoton absorption processes to occur, assist and expand spatial characteristics and conversion procedures wherein a specific wavelength is desired, for specific application. By introducing additional oxidant, oxidation agents, and reactive species, photo reactive scintillating, or fluorescence species so as, these in turn are non linear in nature, and cause dramatic increase in the efficiencies and co-efficiencies associated with effective photo treatment, and disinfection, sterilization and bio-security in wide variety of environmental, agricultural, medical, and commercial, domestic, and municipal treatment applications.

While disclosing a creative solution to couple high intensities into the spatial characteristics of the continuum jet water virtual reactor geometries, the method of the present invention offers a methodology for cases wherein external cuts may hinder physiological activity, and may lead for infection, or further complications. Further more, the present invention facilitate photo treatment of surfaces faster then any previous methodology in the field by using photo catalysis, electro catalysis, and hybridization techniques. The novel methodology of the present invention facilitates the protection of large areas from harmful effects of contact with bacteria, or from contact with noxious or poisonous species.

By calibrating the action spectrum (i.e. absorption, transmittance, transparency, refractive index, or refractive index profile of the air/body, air/instrument, liquid or gas encapsulating layer (i.e. the layer "barrier between the surface of the actual instrumentation or body surface, and entering/triggering beams of pulsed light, and the required coupling of light to the surface to be treated, thus taking into account specie specific wavelength interactions of the laser light (source used in accordance with the methodology of the present invention), the present invention offers economical solution using energy efficient methodology, and extremely safe operation procedures, requiring no skill operators, or special complex hardware procedures. The method of the present invention is simple to implement, and includes fully automatic procedures management, so easy integration into already made set up is simplified, and conserve time and energy during integration, installation, and operation procedures.

More specifically, the method of the present invention by using for example, a pulsed, high repetition rate, high peak power laser light sources, facilitates the formation of high energy density zone through which liquids, or gasses carrying contamination, or may be penetrated by invading antigens, are thus treated according to the methodology of the present invention.

One best mode among the many utilizing the method of the present invention is especially beneficial for disinfection of wide variety of medical instrumentation.

Further more, the methodology disclosed by the present invention offers solution for medical procedures requiring short working cycles, and thus offer important benefits in terms of shorter duty cycles, faster processing time, safer inactivation/dissociation effectiveness, and important capital savings due to the novelty of the methodology of the present invention for photo catalytic protection of medical instrumentation or surfaces, or dimensions, or volumes by using UVA, UVB, UVC light produces by high repetition rates, high peak power lasers, lamps and wide variety of hybrid integrations.

The method of the present invention also relates to detoxification and sterilization of surfaces from dangerous bacteria and chemicals contaminating the surface either through normal application or by hostile action (when used not for aseptic filling but for NBC decontamination applications (not shown). The principle is combination of UV/VIS light with photo catalytic materials in the context of a real time flowing liquid waveguide of the present invention. The chemicals (oxidants, photo catalysts) will be sprayed/scattered (Etc) in the form of liquid solution or suspension stream or droplets or cloud (Etc) from one or more containers, with the light pulses synchronized so that illumination reaches the active chemicals in the right place (at or near the surface) at the right time. Pretreatment of surfaces with non-volatile materials such as $TiO_2$, $ZnO$ etc is another mode of application of the various components of the invention.

Modern technology has failed to provide adequate coating techniques able to provide efficient reflection for commercial applications. Furthermore, most coating reflective efficiencies often not exceeding the 30% mark respectively when wavelength is below the 270 nm. As progress in microelectronics, hydraulics, laser pumping architectures, cooling, pneumatics, and photochemistry yield more accurate diagnostic tools, and software based ray tracing and time analysis, the methodology according to the present invention disclosed a novel proven conceptual design criteria, not available before in any conventional reactor design's historical track record. The method of the present invention which surpasses these limitations imposed by conventional technologies is making available to engineers, producers, scientists, and end users, managers and quality controllers a flowing light guide with plasma coupling centre facilitating efficient light coupling to variable changing refractive index profile driven virtual reactor geometry made out of water, or liquids and gases combinations. This unique coupling ensure optronic efficiencies not available in conventional lenses driven coupling optics (ref 1:A-Z) wherein high average power, high peak power, intensity driven UVA, UVB, UVC pulsed laser photo induced chemistry is efficiently generating free radical species, or oxidizing, or dissolving and/or dissociating and wherein the actual flowing liquid light guide is made of or complimented with or mixed with photo catalytic substances, and elements which once activated greatly increase the efficiencies associated with the photochemical task or application device interoperability and interconnectivity needed to achieve repeatable, standardized operation. Such operation is aimed at the protection of public health, and the environment.

The method of the present invention is especially beneficial for environmental protection applications such as: Sterilization of surfaces and volumes, tools, and interfaces, devices, and global system methodological architectures, disinfection, laser beam management, lithographic processing and optical spatial processing for the deep UV. Such applications may include the need for thermal management, and temperature gradient which may effect material selections, procedures, and design criteria's. The methodology of the present invention may be used to solve many industrialize, agricultural, domestic, medical, infrastructural, economical, and technological challenges given the fact that the cooling element itself (the liquid, gas combination) is the medium in which the light propagates thus substantially increasing cooling efficiencies associated with the need to evacuate heat from a predetermined area, space, volume or boundaries of conventional optical elementals (such as used in conventional disinfection reactor geometries orientations.

The technique of the present invention can advantageously be used in the production of multiphoton absorption processes, and thus provides solution in water and aquaculture treatment sites, mass production of bottled mineral waters, microlithography applications, chip manufacturing sites (water, air, lithographic, TOC reductions, TX reduction, UPW) and food, drink, and beverages industries. The methodology of the present invention also increase the efficiencies associated with conventional treatment technologies and surface and volume photo treatment applications. Further more, the type of free radical species (OH*) which accelerates the reaction rates during treatment operation are produced according to the methodology of the present invention in a controllable, amplified, logged, and monitored multiprocessing reaction processes forming a platform for unique high intensity radical jet trajection spatial workstation in situ with fusion abilities to produce high intensity radiation within a predetermined space and/or variable liquid or gas geometries over a predetermined period of time.

Recent activities in solid state electronics, lasers, and advanced polymer for optronic, laser pumping architectures, all have contributed to production of light sources small enough to be incorporated, or integrated into system in close proximities to bottles, lids, corks, packaging production processes, and wide variety of packaging for foods, drinks, and many biotechnology products, and applications. More specifically the benefits of the method according to the present invention may be implemented in many treatment applications of water, or air, aquaculture, and UPW, drinking, recycling, reclamation or beverages, and mineral water production sites. The methodology of the present invention implements evolution of waveguide technology, and production techniques for creating refractive index profile design in flowing liquid waveguide for partial, or total internal reflection therein for equalizing the concentration of bacteria, viruses, cysts, pathogens, or biological, or organic, non organic, or toxic or noxious species therein (in the flowing liquid "virtual" reactor geometries). Major benefit according to the methodology of the present invention is wherein the flowing liquid light guide is providing in situ continuous cooling to prevent thermal damage to system elements.

The method of the present invention also relates to detoxification and sterilization of surfaces from dangerous bacteria and chemicals contaminating the surface either through normal application or by hostile action (when used not for aseptic filling but for NBC decontamination applications (not shown). The principle is combination of UV/VIS light with photo catalytic materials in the context of a real time flowing liquid waveguide of the present invention. The chemicals (oxidants, photo catalysts) will be sprayed/scattered (Etc) in the form of liquid solution or suspension stream or droplets or cloud (Etc) from one or more containers, with the light pulses synchronized so that illumination reaches the active chemicals in the right place (at or near the surface) at the right time. Pretreatment of surfaces with non-volatile materials such as $TiO2$, $ZnO$ etc is another mode of application of the various components of the invention.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIG. 1 is a schematic illustration of a real time flowing liquid waveguide according to the invention for guiding UVA, UVB, UVC light from a water projection means to produce a UV jet stream;

FIG. 2 exemplifies a system utilizing the technique of the present invention;

FIGS. 3A and 3B illustrate devices formed of an array of UV-jet for aseptic filling using the method of the present invention;

FIG. 4 shows a cross sectional view of a device of the present invention for photochemical treatment through a jet stream of light transmitting liquid; and FIG. 5 illustrates the use of the present invention in a hydrodynamic nozzle projecting a liquid jet stream having a trajectory terminating on a target site.

DETAILED DESCRIPTION OF THE INVENTION

The present invention discloses a novel methodology for creating a real time flowing liquid waveguide or photochemistry.

Referring to FIG. 1, there is schematically illustrated a device 100 according to the invention presenting a real time flowing liquid waveguide for guiding pulsed UVA, UVB, UVC light from a water projection means producing a UV jet stream. The device 100 comprises an elongated (tube-like) hollow body of the UVJET water projection means 1 having first and second inlet ports 2 and 4 and an outlet 14; and a hollow conduit 5 (full of air, or gas) installed in the body 1 so as to project from the body 1 by its pre-pipe portion 6 and define a region 9 inside the body 1 where substances coming from the conduit 5 and the region of the body outside the conduit meet each other. The inlet 2 has the appropriate outer rim diameter (e.g, smaller then the 5-gallon container inlet/outlet) and serves for receiving a laser beam 8 (UV radiation) propagating from a laser device (not shown) in a direction 7 towards the device 100. Here, the laser beam is considered as an output of the laser of a diameter containing 86% of the output power. The inlet 4 serves for inputting water (or another liquid or liquid and gas combination). In the region f the body 1, the UV radiation is coupled to the water stream and this UVJET stream is output from the body 1 through the outlet 14. The water inlet 4 is positioned further along the jet length so as to form venturi pressure where pulsed up laser beams of light are coupled to the UVJET. The laser pulsed UV radiation have energy per pulse of between 1 mJ to about 10 Js. The laser radiation is preferably of about 266 nm wavelength and is trajected, or projected or guided so as to reach the flowing liquid waveguide outlet accurately, thus being launched into the flowing jet-stream. Once water is pumped at the jet inlet at the appropriate pressure forming venturi pressure, preventing the water from spilling out of the jet, simultaneously the laser beam is coupled to the guiding pre-pipe, reaching the jet-stream as it is output the UVJET body, thus forming a flowing liquid waveguide due to the fact that the refractive index of the flowing water (real time) is higher (1.3) then the refractive index of the surrounding air (1.00). Thus, the output 3 of the device 100 is a water-UVJET stream flowing in air.

The time domain optronic (i.e. sub-microsecond pulse durations) sees the water as standing, thus guiding light, resulting from the Total Internal Reflections (TIR) of laser radiation, through the UVJET flowing stream of water can advantageously be used for washing and disinfection of mineral water 5 gallons containers, bottles, and wide variety of surfaces, volumes, conduits, and chambers in industrial, agricultural, medical, and environmental and industrial disinfection and purification applications, or in places wherein washing and disinfection/sterilization is required simultaneously to save energy, time, and duty cycle, conserve energy, and increase efficiencies, and protect public health and the environment.

The technique of the present invention provides a novel methodology for creating a real time flowing liquid wave guide or photochemistry. The laser (generally, at least one radiation unit) suitable to be used in the present invention is preferably a high-intensity pulsed sub-microsecond laser generating UV light beams from 1 mJ per pulse to about 10 Js per pulse at wavelength of about 266 nm and at pulse repetition rates of between 1 Hz to about 100 MHz. The conduit or chamber 1 is aerobic non toxic water projector integrated with at least one dielectric, semi-conductive or super-conductive link or interface, having at least one inlet 6 (generally, water and light can be input through the same inlet), the outlet launcher 9 shaped for dynamic hydro-optical and photochemical predetermined processing effects, and at least one opening 14 un-hindered for passage of liquids and light simultaneously throughout. Each of these openings in the chamber 1 is equipped with optical input or output having predetermined diameter, acceptance angle and biocompatible or photo catalytically immobilized inner or outer surface area layer or thin film coating and at least one venturi suction point sufficiently large for light to be inserted through said opening passage, and sufficiently small for liquid to remain inside flowing forward in a continuum of laminar or turbulent or combinations flow formats. A predetermined volume of liquids or gasses or combinations is simultaneously pumped through the inlet (4 in the example of FIG. 1) of the water projection means to be processed or triggered by the interactions of the guided light. The jet stream (at least one stream), having a higher refractive index ($N_1$) of about 1.3 than that of air or gas surroundings ($N_2$ of about 1.00), is launched forward simultaneously such that the jet streams form a refractive index profiles $N_1/N_2$ with the surrounding, adequate for guiding pulses of UV light by total internal reflection. The UVJET-water stream is guided or delivering projected and simultaneously fills packaged liquids, or allows for sequentially spatially processing the pulses of light and liquid therein, and the pulses and liquid are throughout or distributed directionally to a predetermined surface target site or to the liquid package having a refractive index ($N_3$) lower or higher than the flowing liquid light waveguide (namely higher than $N_1$ and $N_2$. The jet stream may contain at least one bubble. A continuum of predetermined volume of the liquids and gases is simultaneously delivered to the outlet launcher positioned further along the hollow water projection means, at a predetermined pressure volume and/or flow rate sufficient for the formation of at least one venturi pressure point at the non hindering opening, thereby eliminating the need for solid state optical grade elements or lenses, reducing the number of elements in the optical path length from air through water to surface, reducing attenuation, increasing damage threshold, reducing periodical maintenance and replacements. A predetermined oxygen concentration, or singlet oxygen species, or predetermined oxidizer, or photo-catalytic semi conductive metal, or metal oxide particles, or nano porous, or non porous multi-components or semi conductive or dielectric combinations, is added or subtracted to the flowing liquid jet stream proportionately so as to form radical species, or to cause photolytic or photo catalytically triggering or to directly photo chemically affect disinfection, or to sterilize, dissociate, mineralize or oxidize, clean or decontaminate the liquid or gases or surfaces or combination in a single simultaneous action within a predetermined period of time.

The method of the present invention also relates to detoxification and sterilization of surfaces liquid or gases from dangerous bacteria and chemicals contaminating the surface (or volume) either through normal application or by hostile action (when used not for aseptic filling but for NBC decontamination applications (not shown). The principle is combination of UV/VIS light with photo catalytic Materials in the context of a real time flowing liquid waveguide of the present invention. The chemicals (oxidants, photo catalysts) will be sprayed/scattered (Etc) in the form of liquid solution or suspension stream or droplets or cloud (Etc) from one or more containers, with the light pulses synchronized so that illumination reaches the active chemicals in the right place (at or near the surface) at the right time. Pretreatment of surfaces with non-volatile materials such as TiO2, ZnO etc is another mode of application of the various components of the invention.

At least one UV beam of pulsed sub-micro second laser light from at least one radiation unit, having a high intensity peak power source of light, is inserted into or coupled to at least one venturi input of a biocompatible UV water or liquid jet projector means. One or more pulsed UV laser beam can be fiber driven to or directly exposing one or more inputs (e.g., array of such inputs). The JET streams from liquid or water has a refractive index $N_1$ of around 1.3 (e.g., $N_1$=1.33). A predetermined volume or flow rate from this water or liquid jet stream (N1) is projected forward hydro dynamically and hydro-optically into air having a refractive index $N_2$ of about 1.00, and then onto a certain surface (target) having refractive index $N_3$, such that the water or liquid jet stream has sufficient geometrical angular integrity to form a refractive index profile with its surrounding air or gas. The sub microsecond pulsed UV beams are guided therein and throughout by total internal reflection TIR forming high energy density zones (HEDZs) increasing fluence rate and geometrical utilization of the jet stream. The water or liquid, air or surface or combination is exposed to a predetermined spectral distribution over predetermined space over a predetermined period of time from the radiation unit for processing said water or liquid, air or surface to be cleaner more hygienically orientated, biocompatible ensuring more innocuous, more manageable form eliminating noxious species. This technique is especially beneficial for performing aseptic filling and for washing and sterilization of complex surface curvatures simultaneously on a single platform, as well as especially beneficial for defense applications wherein washing and sterilization and advanced oxidation processes are interwoven into the interoperability and interconnectivity of the UVJET platform according to the methodology of the present invention.

The present invention eliminates the need to use hardware type reactors, such as cylindrical conduits or chambers for photochemistry and thus saves on reflecting coating of inner surfaces. The present invention eliminates periodical maintenance and replacement associated with conventional optical elements. By eliminating the use of conventional optical elements such as lenses which are subject to damage threshold optically, the method of the present invention discloses means by which UVJET devices using the method of the present invention perform photolytic and photo catalytic processes thus increasing biocompatibility and processing ability therein (in the UVJET, or throughout the UVJET, VISIJET, or EX-RAYJET), or combination thereof.

The present invention reduces and eliminates the need to use conventional optical elements, hence the venturi pressure and suction point at the back of the UVJET water projection means of the present invention. By manipulating the pressure above a certain threshold the pulsed UV laser beams are inserted at the center of the venturi point thus no lenses are required and no additional optical grade elements are needed, no liquid is spilled out due to the venturi suction. This ensures that the periodical maintenance and replacements associated with conventional sterilization methodologies have been substantially reduced using the method of the present invention and a more streamlined optical design (such as that of the UVJET) contains much less optical elements in the beam path reducing losses and removing the barrier of damage threshold allowing the use of much higher average powers, peak powers or combination thereof.

The radiation unit may include an Argon laser, namely, a laser filled with argon gas. It gives off green and blue light. The strongest lines are at 514 nm (green) and 488 nm (blue) argons range from small 15 milliwatt 110 volt air-cooled models to large 50 watt 440 volt water-cooled systems. Argon lasers are the most common type of light show lasers since they provide unable brightness at a reasonable cost.

The radiation unit may include an axial-flow laser, which is the simplest and most efficient of the gas lasers. An axial flow of gas is maintained through the tube to replace those gas molecules depleted by the electrical discharge used to excite the gas molecules to the lasing state.

The radiation unit may include a $Co_2$ laser, which is widely used in industry and in which the primary lasing medium is carbon dioxide.

Most lasers welding is done with a shield of inert gas flowing over the work surface to prevent plasma oxidation and absorption, to blow away debris, and to control heat reaction. The gas jet has the same axis as the beam so the two can be aimed together.

The present invention may utilize coherent light, namely radiation composed of wave trains vibrating in phase with each other. Coherent light waves all travel the same direction (spatial coherence) at the same frequency and in phase (temporal coherence).

Depth of field (namely, the working range of the beam, a function of wavelength, diameter of the unfocused beam, and focal length of the lens) is adjusted to achieve a small diameter spot size, and thus a high power density. To this end, a short depth of field is accepted.

Water laser in the context of the present invention means the creation of lasing in the water (i.e. while flowing), thus harnessing the flowing liquid wave guide for the formation of a flowing light guiding cavity which could be utilized to create a water laser.

Photochemical effects in the context of the present invention means effects that occur from long exposure durations at incident power levels insufficient to cause damaging photo thermal effects. It is an energy dependent process (a function of the total quantity of radiation absorbed rather than its rate of absorption).

Currently, solid-state lasers are too expensive for most light show uses. This may change over the next few years. The most promising solid-state laser uses a material called nd:YAG, which produces infrared light. This can be frequency doubled (second harmonic generation) to produce up to 60 wafts of green light at 532 nm. The green light can again frequency doubled (fourth harmonic generation) to produce up light at 266 nm, up to several watts.

A medium (environment) to be processed (treated) by the technique of the present invention may be the content of a bottle, conduit, or chamber, for example such as beverages, wine, medical preparation, juice, drinking water, mineral water, insulin products or medical preparation. Spring water, flavored water, flavored beverages, biological traceable compounds, Drug delivery using water based, and/or expanded or flavored water drinks containing vitamins or nutrients, alcohol, blood products, plasma products, air products, gases for propelling medications, sprays, or any liquid or gasses or hybrid combination thereof.

The present invention may utilize a high peak power laser of the Nd:Yag, or Nd:Glass, or Nd: YLF, type or any combination thereof driving the UVJET, or spatially processing pulsed laser light therein, or throughout, or triggering advanced oxidation processes using oxidizers, or using photo catalytic components such as metal oxides ($TiO_2$, $ZdnO_3$, ITO), or predetermined concentration of singlet oxygen, or oxygen concentration, or $O_3$ ozone, or peroxide or combination and operating in the Fourth Harmonic generation mode (i.e. FHG).

A solid state laser (i.e. Nd: Yag type for example), working in the Third Harmonic Generation mode (i.e. THG), may be utilized. An electrical discharge laser such as an excimer laser operating in wavelength from about 193 nm to about 308 and 351 nm, can be utilized.

Each of the pulses of light is aligned into the content of the bottled liquids or gasses for purifying, disinfecting, and ensuring that DNA, and RNA replication sequences are thus inactivated, providing a non invasive disinfecting methodology wherein light pulses from the laser are penetrating the material from which the bottles, (i.e. conduits or chambers, or bottles, or pipes) are made.

A preferred mode for operation of the UVJET is wherein the wavelength of the pulsed sub microsecond laser is about 266 nm, and wherein energy per pulse is from about 1 mJ to about 10 Js, and wherein pulse repetition rate is between about 1 Hz to about 100 MHz and wherein repetition rates or energy density or cumulative energy per $Cm^2$, or average energy or peak power is selected to fit different applications requiring different doses of energy, and subsequent different volumes of liquid to be simultaneously delivered using the methodology of the present invention.

Generally speaking, the laser light source is selected from the following: gas discharge laser, diode pumped lasers, plasma discharged lasers, solid state lasers, semi conductor lasers, crystal type of lasers, X-rays pumped lasers, E-beam pumped gas lasers types, or any combination thereof.

Free Electron Laser (FEL) amplifier), or Electrostatically Accelerated Free Electron Laser (EA/FEL), or organic laser types or any combination thereof can be used.

The laser light source may be tunable from about 1 nm to about 3000 nm, or from about 333 nm to about 360 nm. The peak power density of individual pulses reach from about 1 nJ/Cm2 to about 50 Js/Cm2. The pulsed laser light source may pulse at repetition rates from about 1 Hz to about 300 MHz.

The present invention is suitable for wide ranging application involving different packaging materials, thus their specie specific optical calibration standards are calculated for a specific biodosimetric value or curve to appropriately correspond (being lower) with damage threshold of the substrate material used in a specific application, or tool, or device.

Examples of using the present invention especially beneficial for biomedical application, dentistry and periodentistry applications aimed at implementation and for improving the hygiene of the mouth, may include the following: harnessing the illumination or irradiation of a wave guiding dielectric brush [WDB] containing a sub-miniature version of the UVJET of the present invention. Light is delivered to the UVJET via optical fibers or via direct optical stirring means embedded in an integrated arm having delivery capacity from about one quarter of a million of photons per Cm2/Second to about 999 trillion photons per Cm2/second. Light is delivered to the brush via at least one optical fiber waveguide delivering at least one pulse having peak power or pulse width of between about 7 picoseconds, to about 100 Femtoseconds. Such a brush may be driven via direct laser exposure to its input. The brush may be comprised of a plurality of sub-miniaturized jets according to the invention. Such brush may take the form of a UVJET, visijet, ex-rayjet, or any combination thereof. This is especially beneficial for dentistry applications and for periodentistry for purpose of cleaning pluck formation and for sterilizing and cleaning, washing and disinfecting the inner cavity space and root canals of the mouth or teeth.

The operation of the UVJET may include coupling of high intensity sub-microsecond pulses of laser light to the venturi suction of the water projection means (UVJET, VISIJET, EX-RAYJET, IRJAT, NIRJET), such that no conventional optical elements are required. The EMRJET is driven by at least one pulse having wavelength of about 266 nm and pulse duration or width extending from about 0.1 microsecond to about 100 Atoseconds, with the pulse repetition rates extending the range from between 1 Hz to about 1 GHz (one hertz to about one Giga hertz) to suit adaptation of the real time flowing liquid waveguide to different applications in accordance with the methodology of the present invention. Another suitable mode for operation is wherein light is diffused prior to entering the venturi input suction or light is diffused on entry to the JET stream, or during transversing of the jet stream, or at the end of the jet stream or any combination thereof. Yet another mode for operation is wherein multi line laser is coupled to the jet such that more than one wavelength of light may be used simultaneously. This is beneficial for triggering photo reactive components in the jet stream, or for optical marking of the treated area, especially when treating surfaces.

An arrays of UVJET may be driven by at least one high intensity, high repetition rate laser engine for providing aseptic filling for the bottled water and agro-food industries replacing conventional heat based pasteurization processes, reducing their capital costs and providing substantial reduction on periodical maintenance and replacements. Using wavelength of about 266 nm which sits right on the most sensitive action spectrum of DNA (i.e. the Thiamin base in DNA Davidson at al 1969), provides for aseptically filling, washing and disinfecting simultaneously bottled water, flavored water, beverages, juices, drinking water, water for washing, water for cooling, water for heating, blood and bodily fluids (when sub-miniaturized devices using the method of the present invention), for chemical plants, for pharmaceutical production lines, desalination plants, water treatment plants, metropolitan areas in need of cleaning and sterilization from biological contamination, surface areas in need of advance oxidation treatment (AOT).

Advanced Oxidation Technology (AOT) processes for treatment of liquids, gases and surfaces such as applying hydrogen peroxide (H2O2), ozone, electron beam, UV light etc. are well known. A wide variety of organic contaminants and noxious species of biological origin can be oxidized by AOT. AOT of organic pollutants usually involves hydroxyl radicals as active intermediates, although biological systems may be inactivated by active excited states produced upon direct or indirect light absorption (photosensitization). Photocatalytic oxidations using metal oxides such as TiO2 for decontamination have drawn considerable interest in the last decade for the purpose of cleaning surfaces, water and air.

It is well known that addition of H2O2 to suspension of TiO2 in water, may improve the photocatalytic oxidation efficiency. This results from the conversion of TiO2 electrons to OH radicals, thus increasing the yield of *OH by both retarding electron-*OH (or hole) recombination and supplying additional *OH radicals by the reduction of H2O2. (Upon accepting an electron the H2O2 molecule dissociates into *OH radical and hydroxyl ion (OH—)).

Although many AOT seem to be highly promising for practical applications, the combination of yields, process rates and cost require improvement of processes efficiency, stability and reproducibility. It is widely accepted that without such optimization, commercialization of the promising technological principles will not be forthcoming. More specifically, substantial resources have been assigned to try and locate materials and techniques for improving the geometrical utilization efficiencies in conventional advanced oxidation and photocatalytic reactors.

The present invention concerns the combination of UV light with other advanced oxidation processes, applying, for example, 266 nm laser UV light at relatively long distances or at hidden volumes and surfaces.

Furthermore, attempts to use materials such as HGFS (High Grade Fused Silica) SFS (Synthetic Fused Silica) or other thin film techniques as light guides often foul as these often get clogged or can be covered by colloidal deposit and hard water mineral deposits causing hot spots and deterioration of optical performance.

Such deterioration does not occur using the methodology of the present invention as it is the UVJET boundaries (water/air) which are used to reflect light within the jet stream itself making a virtual reactor type, not hindered by conventional material limitations.

Furthermore, the water jet involves continuous renewal of the liquid/air interface and therefore contamination and foul of the surface is minimized. Furthermore, research and commercialization works conducted to date in the arena of advanced oxidation and photocatalysis often use UV lamps requiring optical elements, which are themselves subject to damage threshold and deterioration of optical performance after prolonged use, or wherein the energy density is high. The method of the present invention surpasses these limitations by inserting high power pulsed sub microsecond UV laser light into the venturi suction point on the water projection means such that no conventional optical lenses or optical elements are needed. This increases the energy, which can be coupled to a single platform and remove damage threshold limitation.

An oxidizer such as H2O2 and/or photocatalyst materials such as TiO2, ZnO, ITO (XXdelete ITO) and other semiconducting metal particles or suspension can be added to the real time flowing liquid waveguide prior to, during, or after or in combination to the launching of the UVJET stream into air, or wherein directionally applying said UVJET stream onto a predetermined surface target site. This allows the methodology of the present invention to activate or initiate the oxidation or photocatalytic processes within the jet stream, or (better) at the tip of the jet stream for surface or volume treatment. Light can be introduced into the jet or be projected externally at specific point along the jet stream. When UV laser pulses are introduced (sub-microsecond pulsed UV laser beams for example) to the flowing jet stream bouncing and reflecting within the jet stream by total internal reflection TIR due to refractive index of liquid being higher than that of the surrounding.

As a result of the refractive index profile thus created, UV pulsed laser light undergoes multiple reflections within the jet stream, which contain the oxidizers or photocatalyst materials, and thus within the angular limitation for the coupling and delivery or guiding of light therein, the method of the present invention provides a unique geometrical utilization using no hardware type reactor vessel, eliminating head-loss associated with conventional reactor types and eliminating the need to search for appropriate reflecting coating which does not exist sufficiently efficient for such deep UV wavelength of light, such that ensures appropriate absorption by oxidizers, semi conductor metal oxides.

Therefore the method of the present invention does not suffer from the limitations of conventional light guide systems, when applying AOT is considered. It can be utilized for delivery, initiation and triggering both advanced oxidation processes, and photocatalysis on a single platform wherein no hardware reactor type is needed and the boundaries of the jet eliminates the need to develop reflecting coating for the deep UV substantially reducing the capital cost and periodical maintenance and replacements associated with conventional methods. The present invention may indeed be suitable for using both Advanced Oxidation materials and photocatalytic processes together in line with the unique platform in which geometrical utilization is increased as long as angular optical orientation (such as jet stream angular orientation compared with the coupled/delivered light throughout) is maintained.

The inner walls of the jet are preferably coated with at least one layer or thin film of semi conductor metal oxides such as TiO2, ZnO, ITO in order to ensure no bio-film growth may accumulate, or for ensuring the biocompatibility and cleanliness of the water projection means at all times. More specifically, such coating or film once exposed to the pulsed laser light reflecting through the jet (before it is launched into air or surface) will produce electron holes and subsequent free radical formation having extremely short life times. These free radical species (i.e. such as hydroxyl radicals) are potent ensuring the surface of the inner walls of the water projection means are remaining clean and sterilized at all times during continuous operation. This will ensure continuous industrialized operation without the need to stop operation for cleaning procedures such as conventional CIP procedures in wide variety of industries.

An additional preferred mode for use of the UVJET is wherein 20 ns, 80 MHz laser beam is coupled to the venturi suction input on the water projection means (UVJET) and wherein the jet is washing, disinfecting, cleaning and dissolving, mineralizing and oxidizing noxious species which may contaminate five gallon water or flavored water jugs (20 liters jugs). An additional preferred mode for utilization of the UVJET is wherein washing and filling and sterilization is occurring simultaneously in order to streamline current water production techniques and to provide a continuum of quality assurance process using the UVJET devices according to the methodology of the present invention.

An additional environmentally friendly preferred embodiment of the present invention is wherein the UVJET stream is conducting electrical current or the jet stream or water projection means may be semi conducting or said water projection means or jet stream it is producing is super conducting or dielectric or any combination thereof. A further suitable mode for interoperability and interconnectivity featuring valuable mechanism in which the UVJET of the present invention may be adapted to suit different applications in bottled water industries, biomedical, bio-photonic and environmental or agricultural applications. In the latter (agricultural, biomedical) specially adapted suspensions or mix (i.e. multi components water based suspensions) are passed through the jet stream in order to perform photochemical processes such as sterilization, disinfection, advanced oxidation, mineralization, cleaning and washing, dissociation and excitation, triggering of photo reactive species, or fluorescent species or quenching or completing dangerous oregano-phosphorous species in a single action or plurality of washing sequences or combinations programmable for the purpose of treating human skin, decontaminating it (from biological/chemical contaminants), or for treating larger metropolitan surface area in need of washing and simultaneously sterilizing or oxidizing the contamination into more innocuous, more manageable forms. More specifically, the methodology of the present invention is used for performing both oxidation and sterilization simultaneously, on the same single technological platform. More specifically treatment of chemical and biological species may be achieved using the methodology of the present invention. This is achieved using the principles of internal reflection within the jet stream to trigger photosensitive species, singlet oxygen species, oxidizers such as h2O2 and utilization of semi conducting metals such as TiO2 photo catalyst. The use of TiO2 photo catalyst and similar materials may assist in keeping the inner surfaces of the water projection means clear, clean, sterilized and free of bio-film formation as free radical species are formed on the surface upon absorption of photons having sufficient electron volts (about 3.4 eV for strong effect/absorption of the photo catalyst) to create electron pair holes on said inner surface. More specifically a hybrid combination is proposed for achieving higher efficiencies wherein both: oxidizer species such as h2O2 and photo catalyst such as TiO2 are used together synchronously or simultaneously. Such preferred embodiment may be suitable for deep cleaning actions or for removal of already formed thick layers of noxious species of biological origin, and/or chemical contamination compounded volumes.

The method of the present invention may include variable use of electrical current conducted along the body of the water projection means, peak power of UV light (sub-microsecond to achieve/maximize peak powers) conducted along the jet stream and through the water projection means and combination applied to the external body or geometry of the jet stream (i.e. along the air or gas surrounding the jet stream, refractive index of about 1.00).

A preferred mode for operation of devices using the methodology of the present invention is wherein additional pulsed laser beams are inserted, superimposed, or projected into or onto the jet stream externally from air, or gas. Once these pulsed beams are entering the jet stream from an adequate angle to minimize optical losses (Fresnel reflections and raley scattering type losses) then higher energy density zones are formed within the UVJET streams increasing or decreasing the rates in which predetermined photochemical process are been pursued.

The flowing liquid light guide may contain bubbles for diffusing the light therein, or for reducing the active liquid medium volume to be treated in a predetermined path length optically, or for a specific jet stream length or volume or combinations. More specifically, bubbles may be inserted or added to the flowing liquid wave guide in order to reduce actual treated volume and increase diffusion of the light therein. More specifically said bubbles may be already designed such that they add or subtract from photolytic, or photo catalytic or combination upon interaction with the light prior to the light entering the jet stream, or prior to the light beams entering the water projection means, or after the light is reflecting through the jet stream or any combination thereof. The use of bubbles may include singlet oxygen, hydrogen, nitrogen or any preferred gas having composition or properties appropriate to achieve the desired photolytic, photo catalytic or advanced oxidation processes according tote method of the present invention.

A single laser station may be coupled to a plurality of waveguides (solid state harness of fibers, multi tailed, such as HGFS/SFS/PCF types). This embodiment has a specific advantages as a plurality or set or array of UVJET may be linked via optical fibers such that at the filling point there is 100% electrical safety, yet aseptic filling operation would not have to be disturbed for special CIP procedures or for cleaning or disinfection procedures (i.e. automatic cleaning procedures in almost all agro-food production sites). This unique utilization mode provides a substantial reduction on the periodical maintenance and replacement required for smooth 24/365 industrialized operation.

Light from at least one high peak power, high intensity, high repetition rate laser engine may be coupled directly to a plurality or set or array of UVJET, or visijet, or Ex-rayjet (according to the methodology of the present invention) for surpassing the damage threshold of conventional optical fibers enabling direct coupling of high power pulsed UV laser beams in an array of filling nozzles (i.e. array of UVJET). This will eliminate the need to use conventional heat based pasteurization processes requiring heavy investment in infrastructure and lengthy and expensive preparation and utility support means. The UVJET of the present invention provides an evolutionary step reducing substantially the foot print associated with conventional systems or sterilization and aseptic filling, while providing energy conscious design to maximize production through put while minimizing operational and maintenance procedures.

In contradistinction to the known treatment processes of the kinds specified, the UVJET devices using the method of the present invention provide no damage to the sensitive components present in flavored water or other sensitive liquid which passes through it. For example, while other treatment methodologies using heat or chemicals strongly effect the components in multi components mix or beverage often effecting negatively the flavor, freshness and texture of the liquid to be treated thus reducing its over all quality and shelf life, the UVJET according to the methodology of the present invention provides a capable platform which does not interfere with the delicate and often sensitive components present in flavored beverages, pharmaceutical preparation, biomedical and environmental protection applications. Rather, the technique of the present invention does not cause molecular migration, organoliptic migration and leaves the treated surfaces or volume passed through the water projection means intact. Due to the ability to lock reflecting pulsed laser beam within the jet stream in motion, thermal aberration of treated surface are minimized (the pulse of light in enclosed within the jet stream of water for example during the filling of mineral or flavored water bottles or five gallon jugs). More specifically the jet stream also cools any thermal dynamics caused by the interaction of the peak power of light onto a predetermined surface (i.e. for example: when washing and disinfecting packaged water products for the bottles water industries).

A 10 W average power, pulsed diode pumped UV laser engine may be coupled to at least one UVJET water projection means and multi photon absorption processes occur within the jet stream having energy of more then one mJ per Cm2. A pulse repetition rate into the jet stream or into the water projection means may be between 10 Hz to about 250 Hz. The pulse repetition rates may be between 5 KHz to about 80 MHz. A single laser engine may be used for driving a plurality or set or arrays of UVJET water projection means. A wavelength may be chosen from the effective wavelength range in photochemistry, from between 266 nm to about 1000 nm. Several frequencies of light may be used sequentially or in unison or serially to suit different application and reaction rates according to the method of the present invention. Photo catalytic, photolytic or advanced oxidation processes may be used wherein the wavelength of the delivered light (within the jet stream) is about 266 nm. For polishing and final photo treatment, the wavelength used is preferably about 355 nm in the UV region of the EMR spectrum. The UVJET may be used for treating water intake from municipality, or the UVJET may process spring water or aquifer water, or drinking water into/out of distribution pipe networks, or the UVJET may be utilized for aseptic filling, replacing conventional heat based pasteurization, or the UVJET may be used to wash and disinfect inner surfaces of five gallon water or beverage jugs, or the UVJET may assist in washing and decontamination of NBC procedures and cleaning and disinfection of human skin or metropolitan surface area.

The spectrum delivered in the jet stream may be of the visible range, NIR (Near Infra Red) range, the far infra red, or combination for optimizing a specific application. Conventional fiber optics may be used to drive an array of UVJET for the purpose of facilitating aseptic filling, washing and sterilization simultaneously on the same platform. The UVJET may be used in a sub-miniaturized version to open pluck formation in the main aorta, or in a specific artery or vain or blood vessel (i.e. within small and large blood vessels or veins). For biomedical applications, the UVJET is used to dissolve tumors, and unwanted restenosis or residues using a preferred UPW (Ultra Pure Water) based suspension and photo reactive or photo catalytic components. In addition, for specific treatment using the methodology of the present invention it will be beneficial to use singlet oxygen or any type of oxidizer in order to produce predetermined specific radical species or to provide adequate photolytic dissociation power to cause a specific photochemical interaction, or reaction rate or combination to suit a predetermined specific application (for example: Bottled water and, Biomedical, biophotonics, defense, environmental protection applications and so forth). The liquid carrying electromagnetic radiation may be a medical preparation, suspension or multi-component mix or solution.

The water projection means may be made out of biocompatible metals, polymer, or organo elastomer. The water projection means may be made out of glass or crystal, which is especially beneficial when scaling down the UVJET according to the methodology of the present invention. Such sub-miniaturized version of the UVJET may be especially beneficial in biomedical domain such as for dentistry and periodentistry applications, cleaning the inner cavity space of the tooth, or for removing pluck formation from tooth and arteries using photo catalysis processes using the UVJET real time liquid waveguide according to the present invention.

The present invention may utilize phenton/phenton processes, wherein oxidizer is added to the flowing liquid waveguide (i.e. to the liquid which conducts light throughout). A preferred mode for using such processes as the phenton/phenton process is wherein the laser used is a multi line laser, or wherein several lasers or a single laser harmonically or frequency doubled is utilized. A predetermined specific wavelength of light may be reflected within the jet stream, while the same wavelength or a different wavelength is projected into the jet stream externally so as to suit a specific application or reaction rate within available limitations.

A scale up of the UVJET may be used for treatment of wastewater, water reclamation or for treatment of agro-food production waste discharge. An array of jets (i.e. UVJET showers) may be angularly positioned such that they form showers for washing and disinfection and for advanced oxidation processes treating humans, or machine interfaces which have been contaminated. The laser engine may be a Nd:Yag laser engine using THG, FHG, THG (Second Harmonic Generation, Fourth Harmonic Generation, Third harmonic Generation), wherein its pulse repetition rate is reduced to augment the power per pulse delivered through the UVJET, or arrays of UVJET operating serially, sequentially, or in parallel or in any programmable combination. Taser engine's pulse repetition rates may be increased so as to reach MHz, or GHz class. This may involve using a quasi-CW mode, or mode locked lasers or electrical discharge lasers, or plasma pumped lasers, or electron beam pumped excimers. Selection of the specific laser engine for any preferred embodiment of the present invention will depend on the specific application for which treatment is required.

For opening drains and for unblocking clogging, the UVJET may operate using direct pulsed UV laser projection into the water projection means. Light may be guided into the UVJET using conventional solid state optical fibers, or photonic band-gapped fibers, or photonic band-gapped crystals or combination thereof. The jet stream may be surrounded with compressed air or gas so as to be able to add components to the jet stream or in order to maximize optical efficiencies using the UVJET of the present invention.

The UVJET may be stationary positioned for performing aseptic filling procedures in the water industries, additionally the UVJET may be mobile in order to provide swift response to disaster areas, and for treatment or decontamination of human skin or metropolitan areas in the event of biological or chemical terrorist attack. The UVJET may be also utilized to wash vehicles, working surfaces and key building installation providing automatic treatment for both biological and chemical eventualities.

Light from the laser may pass through an acoustic-optical shutter prior to entering the UVJET water projection means. An acoustic-optical modulator may be used before or after the pulsed laser beams have entered the water projection means such that the spectral distribution over a predetermined volume over a predetermined surface area (i.e. the dose, or dosimeter value for a specific treatment application), over a predetermined period of time is optimized and may be calculated against specie specific concentration or type of contaminants calibration standards using the method of the present invention.

The jet stream may contain at least one fluorescent component or phosphorous components or photo reactive or photosensitive components for performing treatment or for spectroscopic data acquisition aimed at monitoring the processes of the UVJET according to the methodology of the present invention.

Semi conductive and/or metal particles may be present in the jet stream for performing photo catalysis on surface or volume application such as cleaning of medical instruments, disinfection and cleaning procedures of industrial food processing, decontamination processes and sterilization processes according to the method of the present invention.

For photochemistry, such an effect as photon localization occurring in liquid, or surfaces been treated, or both of them may be utilized.

Figure 2:
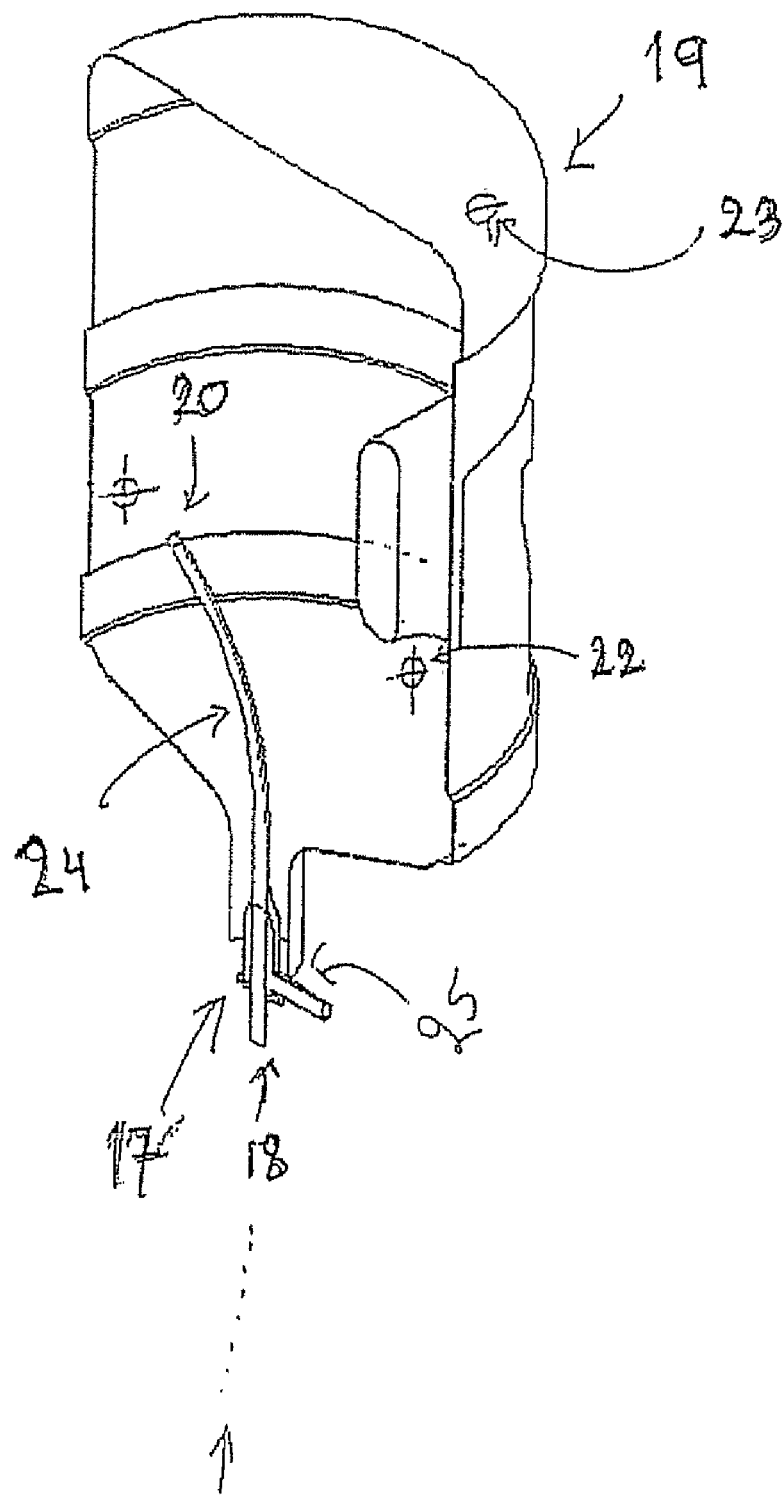

FIG. 2 illustrates how the technique of the present invention can be used for washing and disinfection/sterilization noxious species on the surface of instruments, fruits, in medical, agricultural, industrial, and domestic cleaning, and purification application. In the present example, a device 17 of the present invention (the so-called "water projector") is directly coupled to the inside of a container 19. The device 17 is constructed generally similar to the above-described device 100, and its outlet is inserted into an inlet opening 25 of the container 19. Water stream enters the device through its water inlet 26 while UV pulsed laser light enter through the device light entrance 18. The water stream with the UV light exit together in a common trajectory 24, which is directed either manually or automatically (by means of a production line robot controlling the device) to wash with the water and with the UV light locked within the water streams the entire inner surface of the container, thus hitting noxious species, such as 20, 22, 23, washing them out while eliminating them by means of the UV disinfecting light. The water then may be gathered and recycled by pumping it into the device for further washing sequences. During its flow along the jet the water self disinfecting by the UV, continues. The same small amount of water thus may be utilized, until turbidity is recognized either by human eye or by automatic controlling system, then it may be mixed with fresh water, or be replaced.

The water projecting device may comprise a needle for the insertion of catalysts such as $H_2O_2$, $TiO_2$ into the jet stream at the right point (plasma point, focusing, or collimated trajection of pulsed laser UV light beams).

Figure 3A:
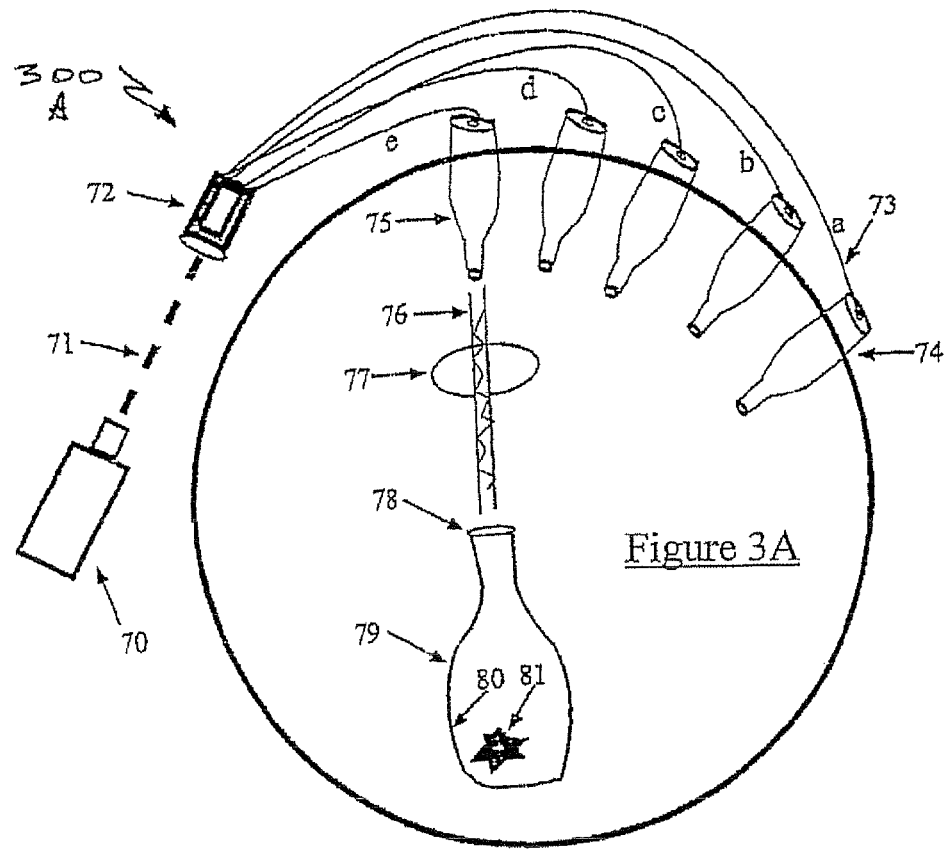
Figure 3B:
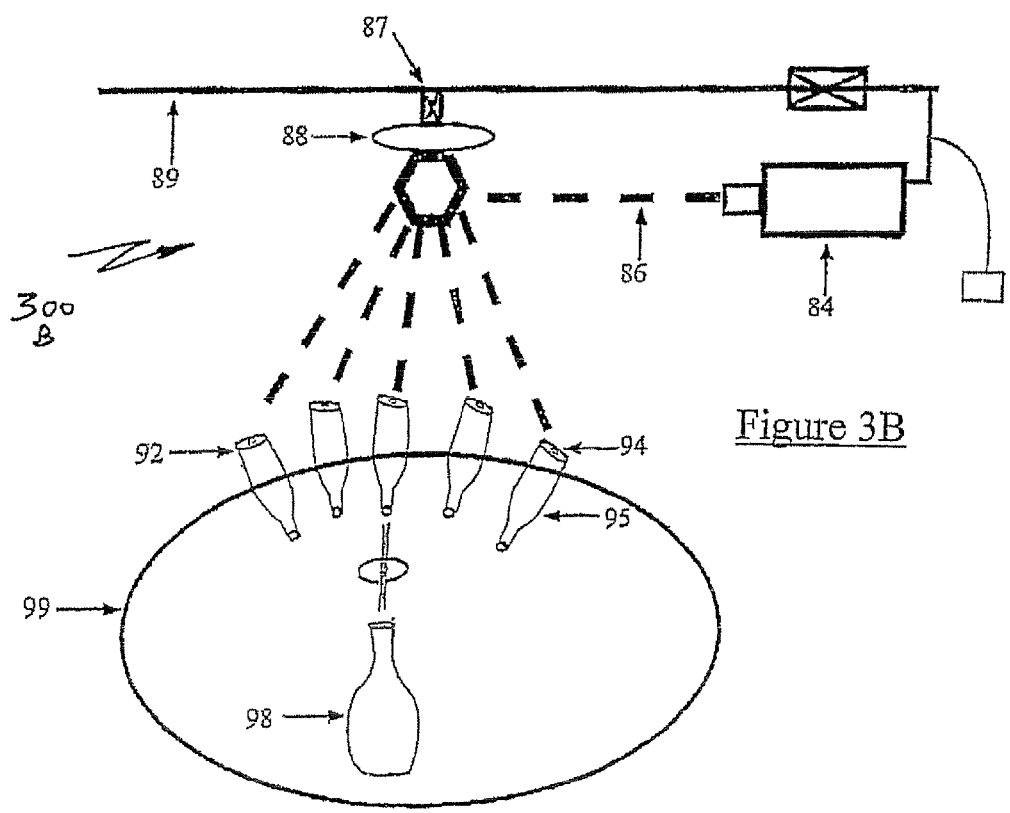

Reference is now made to FIGS. 3A and 3B illustrating the use of the technique of the present invention for aseptic filling or for quality assurance and for industrialized photochemical processing. Here, a system 300 of the present invention comprises at least one radiation unit 70 having a high intensity pulsed sub-microsecond laser generating UV light beams, generally at 71, a multi-tail optical waveguide harness 72 composed of a plurality of optical waveguides (fibers)—five such waveguides 73(*a-e*) being shown in the present example, and a corresponding plurality of hollow aerobic, non toxic, water projection devices 74 of the present invention. The device 74 is a conduit or chamber (having integral conductive, dielectric, semi conductive or super conductive link) having at least one inlet associated with the respective waveguide and an outlet launcher 75. Laser light 71 is thus split by the unit 72 into a respective number of light components (of various or identical energies) coupled to the plurality of waveguides 73, respectively. The light component from each waveguide enters the respective water projecting device 74, where the propagating light is coupled with the flow of an appropriate liquid medium and the light-liquid stream is output at the outlet 75 as a UVJET stream 76 to flow through air (or another gas) environment 77 around the jet stream. This environment 77 has a refractive index lower than that of the jet stream 76 thus enabling the effective (with minimal losses) propagation of the UV light component towards a target—a bottle 79 to be filled with or to be washed by the respective liquid. The UVJET-stream is appropriately aligned with an inlet opening 78 of the bottle. Upon entering the bottle, the UV radiation accesses the inner walls 80 of the bottle thus effecting a predetermined photochemical processing on species 81 located inside the bottle. The inner surface of the UVJET may be coated by a layer of photo catalytic compounds to ensure and maximize biocompatibility and ensure that no bio-film formation will accumulate. Additionally, the UVJET water projection device may be constructed from an already bio-compatible materials not requiring photo catalytic action to remain clean or biocompatible at all times.

The present invention provides for creating an array of real time flowing liquid waveguides for aseptic filling or for quality assurance using photochemistry. As shown in FIG. 3B, at least one radiation unit is provided having a high intensity pulsed sub-microsecond UV laser source 84 that produces a UV light beam 86. The latter is deflected by a stirring mirror or beam deflector, or prism 87, 88, 89 so as to synchronously direct the beams to the inlets 92 of hollow aerobic, non toxic, water projection means 95, 94, 92 of the present invention, where the beams are coupled with liquid streams and are output through outlet launchers towards a conduit or chamber 98 which is a bottle being filled aseptically (the bottled inner surface are being disinfected while said bottle is simultaneously being filled. The bottle 98 is accommodated on a carousel 99 associated with an array or set of UVJET according to the method of there present invention.

Figure 4:
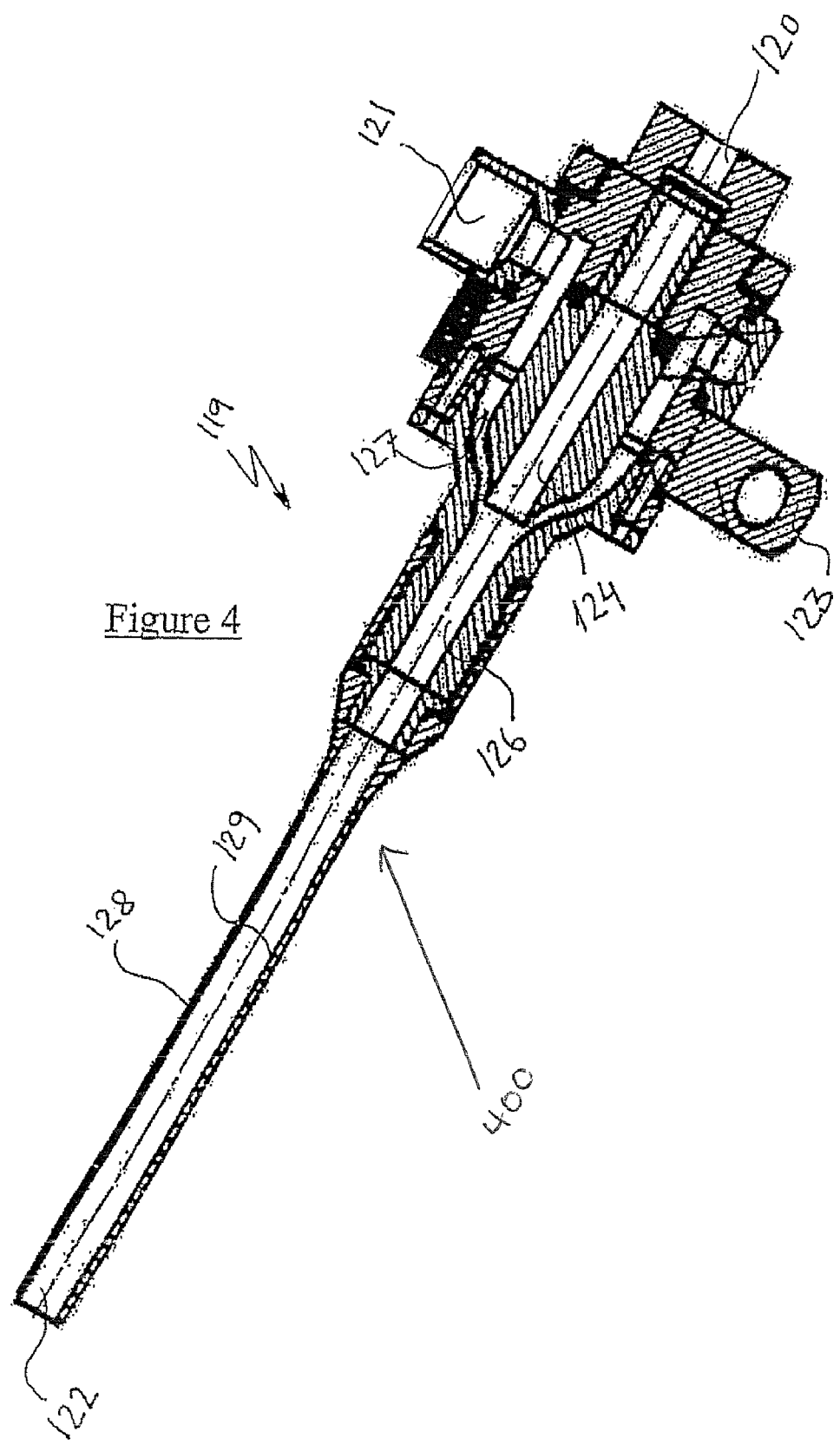

FIG. 4 illustrates a cross sectional view of a device 119 of the present invention for photochemical treatment through a jet stream of light transmitting liquid. The device 400 is configured as a liquid jet stream launcher having a liquid inlet 121 for receiving liquid from a liquid supply means (not illustrated); a liquid projection outlet 122 in liquid communication with the inlet 121; a light radiation inlet (entrance opening) 120 positioned in an appropriate orientation relatively to the outlet 122 for directing a beam of light into the liquid flow such that the beam of light is being guided within a liquid jet stream projected from the liquid projection outlet 122, locked within along the trajectory of the jet towards a target site. In this specific example, the device further comprises a wall bracket 123 useful for anchoring the device to either stationary or adjustable support. Thus, appropriate liquid enters the device via the inlet 121 and is forced towards a flow stabilizer portion 126 through a spherical groove 127 while performing venturi hydrodynamic-pneumatic differential pressure between the liquid path (through the flow stabilizer portion 126) and the light/air passage 124. An air suction operation is performed wherein air entering via the light radiation entrance opening 120 is sucked and mixed into the flowing liquid, thus increasing the diffusion of light within the jet. The inner surface 129 of a hydrodynamic nozzle 128 may be coated with a photo catalytic coating in order to prevent sedimentation during long period use.

Figure 5:
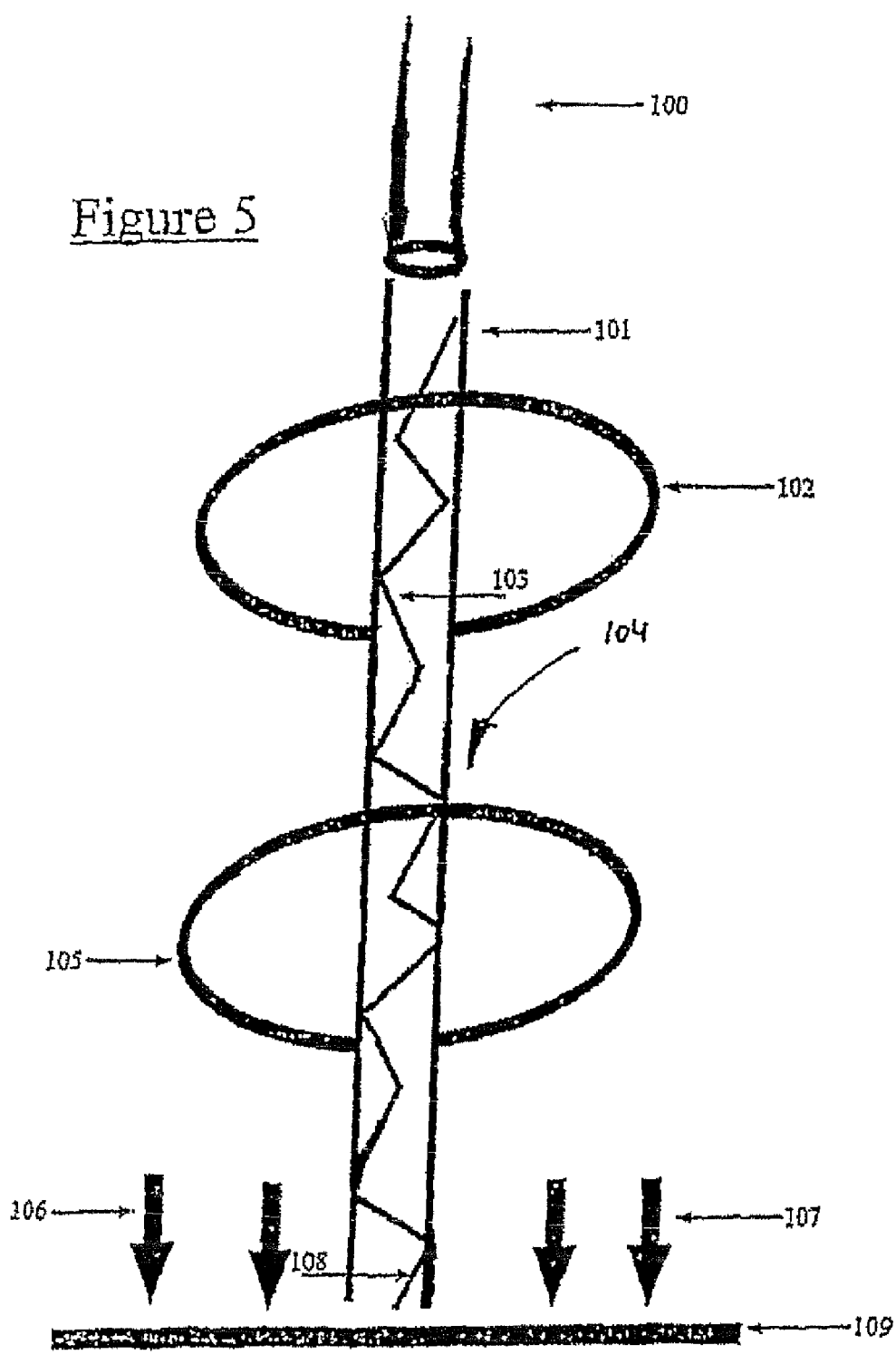

FIG. 5 schematically illustrates a hydrodynamic nozzle 100 suitable to be used in the device of the present invention for projecting a liquid jet stream 101 having a trajectory 104 which terminates on a target site 109 surface. A light beam 103 is being guided inside the jet stream 101, and internally refracted several times along the jet trajectory, however, locked inside and tracing its path until reaching a vicinity 108 of the target site. This is due to the refractive index of the liquid that is greater than the refractive index of the surrounding air 102, and from the refractive index of another surrounding gas (e.g. Argon) 105 (that may be dispersed according to various treatment types in order to enhance the refractive profile). When the jet stream with the light beam hits the target site 109 surface, the liquid is already purified due to the photochemical effects that occur during its flow through the air, however, the target site surface also becomes purified around, as pointed out by the arrow icons 106 and 107. This is due to the scattering of light reflected all around between the droplets and micro droplets created from the jet while hitting the surface.

The following are experimental results obtained with the technique of the present invention, consisting of two disinfecting procedures performed according to the following parameters.

Example 1: refers to disinfecting a contamination of the species *Bacillus Subtilis*. The following conditions were used: initial concentration—$3.9*10^5$ cfu/ml; laser parameters—250 mw average power, 15 KHz pulse frequency, 30 ns pulse duration; water jet flow-rate—500 ml/sec

| Treatment Duration (sec) | Water jet treatment (without UV) No. of bacteria (cfu/ml) | Water jet + UV treatment No. of bacteria (cfu/ml) |
|---|---|---|
| 0 | $3.6 * 10^5$ | $3.6 * 10^5$ |
| 1 | $6.9 * 10^4$ | $1.8 * 10^2$ |
| 3 | $4.0 * 10^2$ | $2.5 * 10^1$ |

Example 2: refers to disinfecting a contamination of the species *Aspergillus Niger*. The following conditions were used: initial concentration—$2.1*10^5$ cfu/ml; laser prameters—250 mw average power, pulsed 15 KHz, 30 ns pulse duration; water jet flow-rate—500 ml/sec.

| Treatment Duration (sec) | Water jet treatment (without UV) No. of bacteria (cfu/ml) | Water jet + UV treatment No. of bacteria (cfu/ml) |
|---|---|---|
| 0 | $3.3 * 10^3$ | $3.3 * 10^3$ |
| 1 | $5.2 * 10^2$ | $1.6 * 10^2$ |
| 3 | $8.0 * 10^1$ | $1.1 * 10^1$ |

In both examples, contamination has been preformed on empty, unused bottles. It was done on-site, using the following protocol:
1. Known stock suspension of bacteria were reduced to contamination concentration as referenced in the tables per each individual specie;
2. 10 ml per container have been used for infection, shaken thoroughly in bottle until uniformly distributed, so that bacteria will reach all surfaces of containers. Access liquid disposed properly.

3. Containers were dried over-night at 34 C oven, and then capped with sterile caps.

Contamination were preformed shortly before the demonstration.

The data in the tables refer to the following three disinfecting runs performed per each bacteria species:
 (i) positive control per each strain, without treatment;
 (ii) treatment by washing cycles of water jet without UV;
 (iii) treatment by washing cycles of water jet with UV thereby delivered.

All tests have been preformed with 2 repeats (to account for statistical variations).

The data in tables 1 and 2 represents the average values of each run.

Sampling of bottles has been preformed using the following protocol:
 1. 50 ml saline has been poured into treated containers, each container than capped with sterile cap;
 2. Capped containers have been shaken so that all surface of the container will be sampled;
 3. Sampled liquid has been poured into sterile collection containers;
 4. Incubation and plate counting of the bacteria have been performed using standard procedures.

Those skilled in the art will readily appreciate that various modifications and changes can be applied to the embodiments of the invention hereinbefore exemplified without departing from the scope defined in and by the appended claims.

The invention claimed is:

1. A method for ultraviolet (UV) liquid disinfection, the method comprising:
 providing a jet stream of liquid to be disinfected by UV-radiation, said liquid including contaminants and said jet stream is surrounded by air; and
 disinfecting the liquid within the jet stream by directing, into said jet stream of liquid, said UV-radiation such that said UV-radiation is being guided throughout said jet stream and the liquid to be disinfected serves as a flowing liquid wave guide for the UV-radiation along the longitudinal trajectory of the jet stream using total internal reflection.

2. The method of claim 1, wherein said UV-radiation is generated by a laser source.

3. The method of claim 1, wherein said liquid having a refractive index greater than a refractive index of a medium surrounding said liquid.

4. The method of claim 1, wherein the UV-radiation being UVA-radiation, UVB-radiation or UVC-radiation.

5. The method of claim 1, wherein the liquid being water or wastewater.

* * * * *